US008475732B2

(12) United States Patent
Simmons et al.

(10) Patent No.: US 8,475,732 B2
(45) Date of Patent: Jul. 2, 2013

(54) ANALYTE MEASUREMENT DEVICES AND SYSTEMS, AND COMPONENTS AND METHODS RELATED THERETO

(75) Inventors: Matthew Simmons, Pleasanton, CA (US); Cherie Bulala, Berkeley, CA (US); Christopher Myles, Alameda, CA (US); Bonita Song, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 13/281,315

(22) Filed: Oct. 25, 2011

(65) Prior Publication Data
US 2012/0100601 A1    Apr. 26, 2012

Related U.S. Application Data

(60) Provisional application No. 61/406,860, filed on Oct. 26, 2010.

(51) Int. Cl.
*G01N 31/22*    (2006.01)
*G01N 11/00*    (2006.01)
*A61B 5/05*    (2006.01)

(52) U.S. Cl.
USPC .......................... 422/404; 600/347; 73/53.01

(58) Field of Classification Search
USPC ....................................................... 422/404
See application file for complete search history.

(56) References Cited

U.S. PATENT DOCUMENTS

| | | | |
|---|---|---|---|
| 4,150,863 A | 4/1979 | Krafthefer et al. | |
| 4,494,809 A | 1/1985 | Soloman | |
| 4,533,202 A | 8/1985 | Pohl | |
| 4,545,382 A | 10/1985 | Higgins et al. | |
| 4,711,245 A | 12/1987 | Higgins et al. | |
| 4,774,192 A | 9/1988 | Terminiello et al. | |
| 4,868,711 A | 9/1989 | Hirama et al. | |

(Continued)

FOREIGN PATENT DOCUMENTS

| DE | 202006013075 | 11/2006 |
|---|---|---|
| EP | 1112717 | 7/2001 |

(Continued)

OTHER PUBLICATIONS

International Search Report for PCT Application No. PCT/US2009/050119, dated Jan. 18, 2010.

(Continued)

*Primary Examiner* — Jill Warden
*Assistant Examiner* — Brittany Fisher
(74) *Attorney, Agent, or Firm* — Edward J. Baba; Daniel G. Stoddard; Bozicevic, Field & Francis LLP

(57) ABSTRACT

In some aspects, a modular analyte measurement system having a replaceable strip port module is provided to permit contaminated modules to be replaced. Some aspects of the present disclosure relate to barriers for strip ports or the sealing of strip ports and/or analyte measurement devices to maintain a clean strip port and/or enable the strip port to be cleaned for reuse. Cleaning tools are also provided. Also provided are strip port interfaces that guide fluid away from the strip port opening, as well as absorptive elements that prevent fluid from entering a strip port. Analyte measurement devices with gravity sensors or accelerometers are also provided, along with methods related thereto. Also provided is a docking station that serves as an information server and provides storage and recharging capabilities.

18 Claims, 37 Drawing Sheets

U.S. PATENT DOCUMENTS

| | | | |
|---|---|---|---|
| 4,911,344 A | 3/1990 | Kahler | |
| 4,940,422 A | 7/1990 | Forish et al. | |
| 5,217,388 A | 6/1993 | Brown | |
| 5,262,035 A | 11/1993 | Gregg et al. | |
| 5,262,305 A | 11/1993 | Heller et al. | |
| 5,264,014 A | 11/1993 | Lannefors et al. | |
| 5,279,294 A | 1/1994 | Anderson et al. | |
| 5,320,715 A | 6/1994 | Berg | |
| 5,356,786 A | 10/1994 | Heller et al. | |
| 5,391,094 A | 2/1995 | Kakinoki et al. | |
| 5,509,410 A | 4/1996 | Hill et al. | |
| 5,526,120 A | 6/1996 | Jina et al. | |
| 5,536,249 A | 7/1996 | Castellano et al. | |
| D376,763 S | 12/1996 | Flora et al. | |
| 5,593,323 A | 1/1997 | Dernehl | |
| 5,593,852 A | 1/1997 | Heller et al. | |
| 5,601,435 A | 2/1997 | Quy | |
| 5,628,890 A | 5/1997 | Carter et al. | |
| 5,705,936 A | 1/1998 | Gibson et al. | |
| 5,708,247 A | 1/1998 | McAleer et al. | |
| 5,820,551 A | 10/1998 | Hill et al. | |
| 5,822,715 A | 10/1998 | Worthington et al. | |
| 5,899,855 A | 5/1999 | Brown | |
| 5,918,603 A | 7/1999 | Brown | |
| 5,925,021 A | 7/1999 | Castellano et al. | |
| D413,537 S | 9/1999 | Grossman et al. | |
| 5,984,690 A | 11/1999 | Riechelmann et al. | |
| 6,071,391 A | 6/2000 | Gotoh et al. | |
| 6,120,676 A | 9/2000 | Heller et al. | |
| 6,121,009 A | 9/2000 | Heller et al. | |
| 6,143,164 A | 11/2000 | Heller et al. | |
| 6,144,837 A | 11/2000 | Quy | |
| 6,161,095 A | 12/2000 | Brown | |
| 6,175,752 B1 * | 1/2001 | Say et al. | 600/345 |
| 6,183,274 B1 | 2/2001 | Allum | |
| 6,268,162 B1 | 7/2001 | Phillips et al. | |
| 6,270,455 B1 | 8/2001 | Brown | |
| 6,281,006 B1 | 8/2001 | Heller et al. | |
| 6,284,478 B1 | 9/2001 | Heller et al. | |
| 6,299,757 B1 | 10/2001 | Feldman et al. | |
| 6,338,790 B1 | 1/2002 | Feldman et al. | |
| 6,377,894 B1 | 4/2002 | Deweese et al. | |
| 6,431,884 B1 | 8/2002 | Wallace et al. | |
| 6,445,350 B2 | 9/2002 | Takenobu | |
| 6,461,496 B1 | 10/2002 | Feldman et al. | |
| 6,503,381 B1 | 1/2003 | Gotoh et al. | |
| 6,506,168 B1 | 1/2003 | Fathallah et al. | |
| 6,514,460 B1 | 2/2003 | Fendrock | |
| 6,514,718 B2 | 2/2003 | Heller et al. | |
| 6,540,891 B1 | 4/2003 | Stewart et al. | |
| 6,560,471 B1 | 5/2003 | Heller et al. | |
| 6,591,125 B1 | 7/2003 | Buse et al. | |
| 6,592,745 B1 | 7/2003 | Feldman et al. | |
| 6,600,997 B2 | 7/2003 | Deweese et al. | |
| 6,616,819 B1 | 9/2003 | Liamos et al. | |
| 6,618,934 B1 | 9/2003 | Feldman et al. | |
| 6,638,716 B2 | 10/2003 | Heller et al. | |
| 6,676,816 B2 | 1/2004 | Mao et al. | |
| 6,679,137 B1 | 1/2004 | Bek | |
| 6,730,200 B1 | 5/2004 | Stewart et al. | |
| 6,736,957 B1 | 5/2004 | Forrow et al. | |
| 6,743,635 B2 | 6/2004 | Neel et al. | |
| 6,746,582 B2 | 6/2004 | Heller et al. | |
| 6,749,740 B2 | 6/2004 | Liamos et al. | |
| 6,764,581 B1 | 7/2004 | Forrow et al. | |
| 6,773,671 B1 | 8/2004 | Lewis et al. | |
| 6,850,283 B1 | 2/2005 | Tatamiya | |
| 6,881,551 B2 | 4/2005 | Heller et al. | |
| 6,881,578 B2 | 4/2005 | Otake | |
| 6,893,545 B2 | 5/2005 | Gotoh et al. | |
| 6,908,008 B2 | 6/2005 | Pugh | |
| 6,940,021 B2 | 9/2005 | Pohl et al. | |
| 6,942,518 B2 | 9/2005 | Liamos et al. | |
| 6,976,624 B2 | 12/2005 | Hsiao | |
| 7,041,468 B2 | 5/2006 | Drucker et al. | |
| 7,077,328 B2 | 7/2006 | Krishnaswamy et al. | |
| 7,167,818 B2 | 1/2007 | Brown | |
| 7,172,728 B2 * | 2/2007 | Otake | 422/404 |
| 7,179,129 B1 | 2/2007 | Hwang | |
| D540,208 S | 4/2007 | Mobley et al. | |
| 7,299,082 B2 | 11/2007 | Feldman et al. | |
| D560,129 S | 1/2008 | Rich et al. | |
| 7,337,918 B2 | 3/2008 | Fowler et al. | |
| 7,488,216 B2 | 2/2009 | Cho | |
| 7,866,026 B1 | 1/2011 | Wang et al. | |
| 7,896,703 B2 | 3/2011 | Stafford et al. | |
| 8,292,180 B2 | 10/2012 | Ehrhart et al. | |
| 8,292,810 B2 | 10/2012 | Goode et al. | |
| 8,301,395 B2 | 10/2012 | Matievich et al. | |
| 8,328,735 B2 | 12/2012 | Haar et al. | |
| 2003/0176183 A1 | 9/2003 | Drucker et al. | |
| 2003/0191415 A1 | 10/2003 | Moerman et al. | |
| 2004/0073095 A1 | 4/2004 | Causey et al. | |
| 2004/0086425 A1 | 5/2004 | Jaunakais | |
| 2004/0094433 A1 | 5/2004 | Neel et al. | |
| 2004/0186365 A1 | 9/2004 | Jin et al. | |
| 2004/0254434 A1 | 12/2004 | Goodnow et al. | |
| 2004/0267300 A1 | 12/2004 | Mace | |
| 2005/0121826 A1 * | 6/2005 | Hajizadeh et al. | 264/239 |
| 2005/0154271 A1 | 7/2005 | Rasdal et al. | |
| 2005/0169810 A1 | 8/2005 | Hagen et al. | |
| 2005/0281706 A1 | 12/2005 | Funke et al. | |
| 2006/0025662 A1 | 2/2006 | Buse et al. | |
| 2006/0030789 A1 | 2/2006 | Allen | |
| 2006/0040333 A1 | 2/2006 | Zocchi | |
| 2006/0091006 A1 | 5/2006 | Wang et al. | |
| 2006/0148096 A1 | 7/2006 | Jina | |
| 2006/0224141 A1 | 10/2006 | Rush et al. | |
| 2007/0068807 A1 | 3/2007 | Feldman et al. | |
| 2007/0095661 A1 | 5/2007 | Wang et al. | |
| 2007/0100222 A1 | 5/2007 | Mastrototaro et al. | |
| 2007/0108048 A1 | 5/2007 | Wang et al. | |
| 2007/0149897 A1 | 6/2007 | Ghesquiere et al. | |
| 2007/0199818 A1 | 8/2007 | Petyt et al. | |
| 2007/0233395 A1 | 10/2007 | Neel et al. | |
| 2007/0247793 A1 | 10/2007 | Carnevali | |
| 2008/0066305 A1 | 3/2008 | Wang et al. | |
| 2008/0099332 A1 | 5/2008 | Scott et al. | |
| 2008/0102441 A1 | 5/2008 | Chen et al. | |
| 2008/0119709 A1 | 5/2008 | Wang et al. | |
| 2008/0148873 A1 | 6/2008 | Wang | |
| 2008/0167578 A1 | 7/2008 | Bryer et al. | |
| 2008/0234559 A1 | 9/2008 | Arbogast et al. | |
| 2008/0267823 A1 | 10/2008 | Wang et al. | |
| 2008/0269673 A1 * | 10/2008 | Butoi et al. | 604/67 |
| 2009/0018411 A1 * | 1/2009 | Mace et al. | 600/309 |
| 2009/0095625 A1 | 4/2009 | Forrow et al. | |
| 2009/0187351 A1 | 7/2009 | Orr et al. | |
| 2009/0255811 A1 | 10/2009 | Forrow et al. | |
| 2009/0270696 A1 | 10/2009 | Arbogast et al. | |
| 2010/0015649 A1 * | 1/2010 | Day | 435/13 |
| 2010/0064800 A1 * | 3/2010 | Stafford et al. | 73/431 |
| 2010/0198034 A1 | 8/2010 | Thomas et al. | |
| 2010/0198142 A1 | 8/2010 | Sloan et al. | |
| 2010/0213057 A1 | 8/2010 | Feldman et al. | |
| 2010/0324392 A1 | 12/2010 | Yee et al. | |
| 2010/0326842 A1 | 12/2010 | Mazza et al. | |
| 2010/0331652 A1 | 12/2010 | Groll et al. | |
| 2011/0040246 A1 | 2/2011 | Galasso | |
| 2011/0184264 A1 | 7/2011 | Galasso et al. | |

FOREIGN PATENT DOCUMENTS

| | | |
|---|---|---|
| EP | 1543935 | 6/2005 |
| EP | 1712910 | 10/2006 |
| EP | 1729128 | 12/2006 |
| FR | 2674379 | 9/1992 |
| GB | 1170256 | 11/1969 |
| WO | WO 2005096446 | 10/2005 |
| WO | WO 2006002432 | 1/2006 |
| WO | WO 2007097746 | 8/2007 |

OTHER PUBLICATIONS

International Search Report for PCT Application No. PCT/US2011/057741, dated Mar. 6, 2012.

* cited by examiner

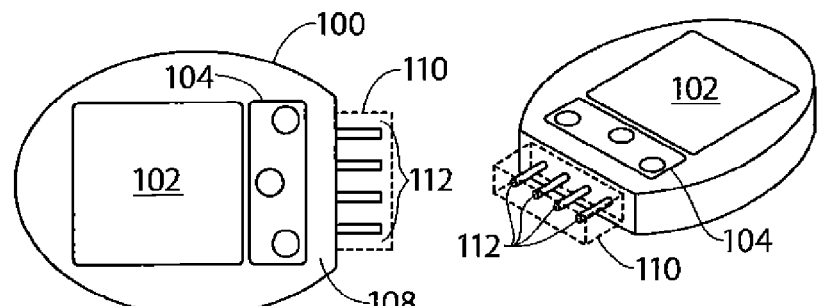
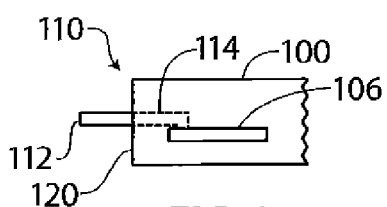 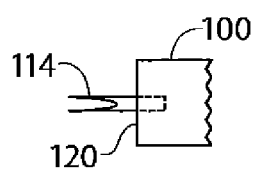 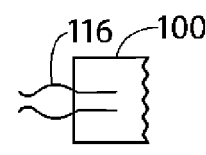
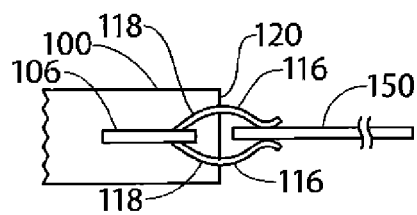 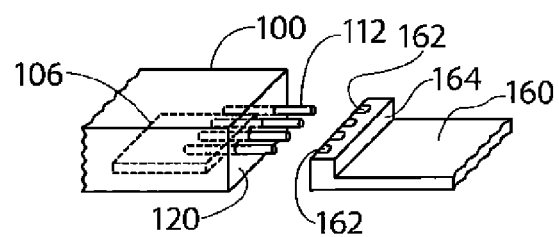
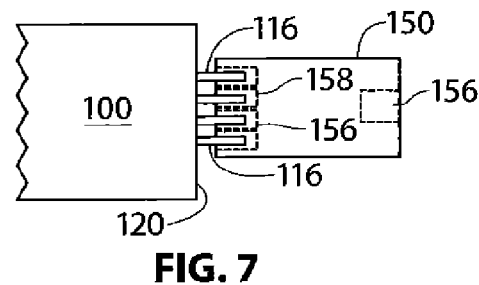 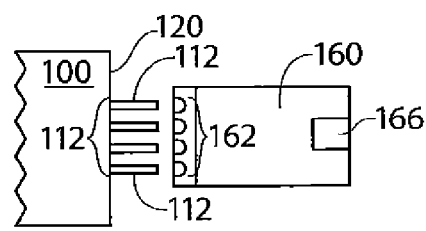

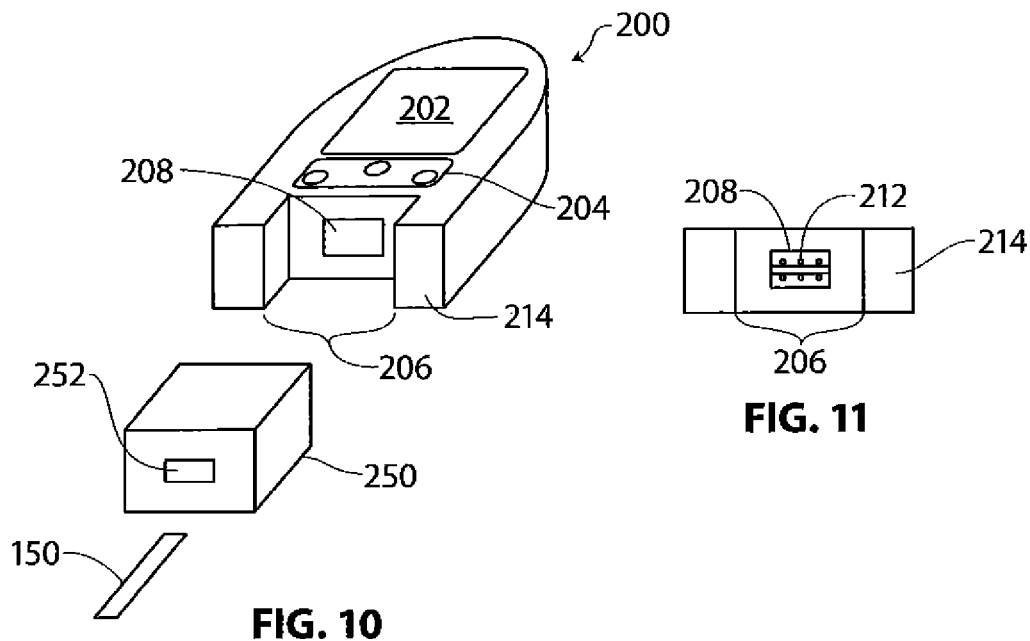
FIG. 10
FIG. 11
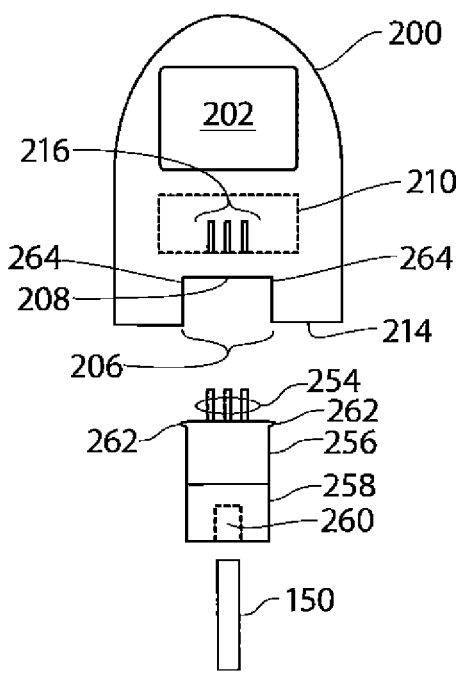
FIG. 12

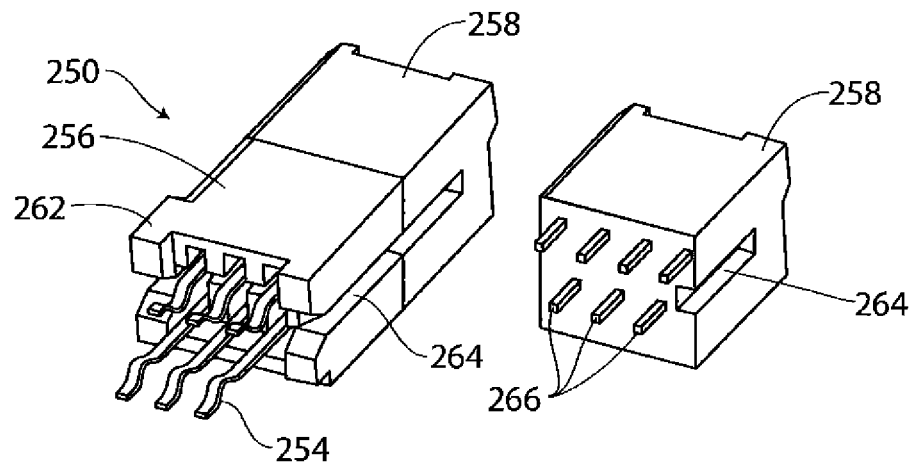
FIG. 13  FIG. 14
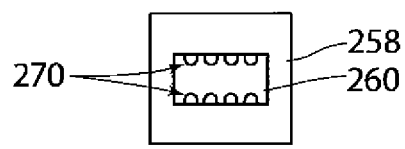
FIG. 15
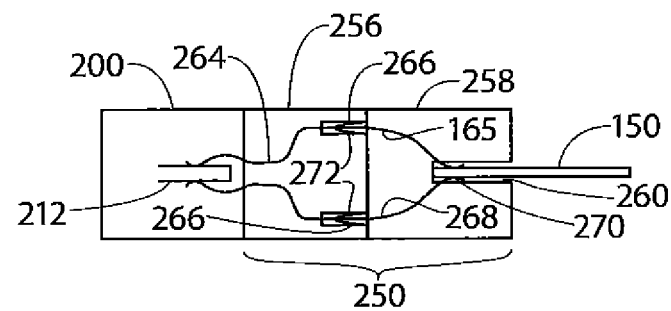
FIG. 16

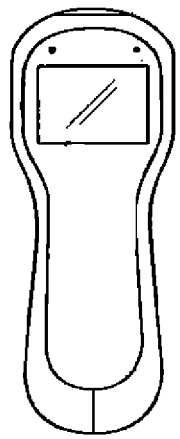
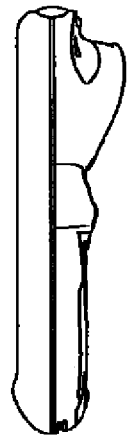
FIG. 34A  FIG. 34B
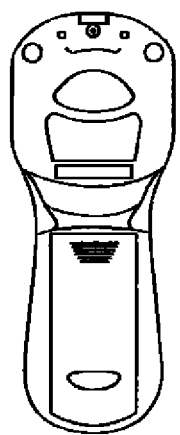
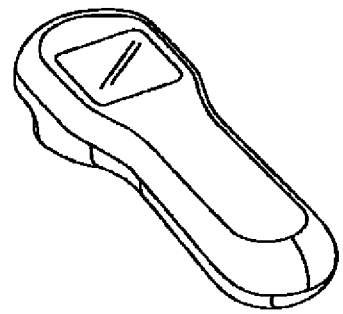
FIG. 34C  FIG. 34D

ANALYTE MEASUREMENT DEVICES AND SYSTEMS, AND COMPONENTS AND METHODS RELATED THERETO

PRIORITY

This application claims the benefit of priority to U.S. Provisional Patent Application No. 61/406,860, filed Oct. 26, 2010, which is hereby incorporated by reference.

CROSS-REFERENCE TO RELATED APPLICATIONS

This application is related to U.S. patent application Ser. No. 12/175,279, filed on Jul. 17, 2008. This application is also related to U.S. patent application Ser. Nos. 12/495,662, filed on Jun. 30, 2009, and 12/624,231, filed on Nov. 23, 2009, both of which claim priority to U.S. patent application Ser. No. 12/175,279. The disclosures of the above-mentioned applications are incorporated herein by reference in their entirety.

BACKGROUND

One of the tools used in diabetes management is an analyte measurement device (or analyte meter). An analyte measurement device is typically used to measure the blood glucose level of a person based on a sample of blood. The process of using an analyte measurement device is not complicated, and is often performed several times a day. First, a user inserts an analyte test strip into a strip port of the measurement device. The user then lances her finger to obtain a small sample of blood. The blood sample is then placed onto the analyte test strip, and the measurement device analyzes the blood sample. The measurement device then typically displays a blood glucose level from the analysis.

In order to ensure an accurate measurement is being generated, it is necessary to keep the measurement device free from contamination. There are instances where the strip port may become contaminated with blood or other fluids (e.g., calibration fluid). When this occurs, the performance of the measurement device suffers and the user is no longer assured an accurate result. As such, the user may need to purchase a new measurement device.

Dedicated hospital meters have high occurrence rates of contamination due to factors such as heavy use, need for calibration, and other environmental factors. Contamination of a hospital meter, and the subsequent need to replace the hospital meter, is costly. Further, the inventors have found that a substantial number of hospital meters are returned to the manufacturer simply because the strip port has been contaminated, while most of the other parts of the meter remain entirely functional.

BRIEF SUMMARY

Presented herein is a modular analyte measurement system having a replaceable strip port module. Some aspects of the present disclosure relate to modular components of the analyte measurement system. In one embodiment, for example, there is provided a replaceable strip port module having a housing and an analyte test strip port disposed within the housing. The module is inserted within an opening in an analyte meter, and is thereafter removably attached to the meter. The analyte test strip port within the module is electrically coupled to the analyte meter. In the event that the analyte test strip port within the module is contaminated, the replaceable strip port module can be removed and exchanged for a new replaceable strip port module.

In some aspects of the present disclosure, an analyte measurement system is provided that includes an analyte meter having a meter housing and a processing circuit disposed within the housing, and a replaceable strip port module. The replaceable strip port module has a module housing that includes a first aperture, which receives an analyte test strip, and an interface aperture. The replaceable strip port module has an analyte test strip port disposed within the module housing, and has an electrical interface coupled to the analyte test strip port within the module housing and extending out of the housing through the interface aperture.

In one embodiment, the analyte measurement system includes an attachment feature to removably attach the replaceable strip port module to the analyte meter.

In one embodiment, the module housing fits within an aperture in the meter housing.

In one embodiment, the module housing includes external alignment features to align the module housing within the aperture in the meter housing.

In one embodiment, the meter housing includes alignment features to align the module housing within the aperture in the meter housing.

In one embodiment, the electrical interface includes a plurality of contact pads to couple to SIM connectors within the meter housing.

In one embodiment, the electrical interface includes a plurality of pins to couple to a pin header within the meter housing.

In one embodiment, the electrical interface includes an edge connector to couple to a corresponding edge connector within the meter housing.

In some aspects of the present disclosure, a replaceable strip port module is provided for use in a modular analyte measurement system, and includes a housing. The housing includes an open end and an interface aperture. The replaceable strip port module also includes an analyte test strip port disposed within the open end of the housing, and an electrical interface coupled to the analyte test strip port within the housing and positioned such that the electrical interface is exposed to the exterior of the housing through the interface aperture, and a cap covering the open end of the housing. The cap includes an aperture sized to receive an analyte test strip, and the aperture is aligned with the analyte test strip port such that when an analyte test strip is inserted into the aperture, the analyte test strip is inserted into the analyte test strip port.

In one embodiment, the housing further comprises internal alignment features to align the analyte test strip port within the housing.

In one embodiment, the housing comprises external alignment features to align the replaceable strip port module within an analyte meter in the analyte measurement system.

In one embodiment, the electrical interface includes a plurality of contact pads configured to couple to SIM connectors within an analyte meter.

In one embodiment, the electrical interface includes a plurality of pins to couple to a pin header within an analyte meter.

In one embodiment, the electrical interface includes an edge connector to couple with a corresponding edge connector within an analyte meter.

In one embodiment, the cap includes an indented region on a surface of the cap.

In one embodiment, a first cap gasket is provided as a seal between the cap and an analyte meter.

In one embodiment, a second cap gasket is provided as a seal between the cap and the housing.

In one embodiment, a single cap gasket is provided as a seal between the cap, the housing, and an analyte meter.

Some aspects of the present disclosure related to barriers for strip ports or the sealing of strip ports and/or analyte measurement devices to maintain the strip port and device free from fluids or other contaminants, and/or to enable the strip ports and device to be cleaned or disinfected for reuse.

In one embodiment, a barrier device is coupled to a strip port to provide for a contaminant free environment.

In another embodiment, the strip port is a replaceable strip port module that may be removably coupled to the analyte measurement device to be cleaned and re-used, or disposed of after contamination.

In yet another embodiment, the strip port is internally sealed to contain fluid within the strip port and prevent fluid from entering the remainder of the measurement device.

In yet another embodiment, the analyte measurement device is partially or completely sealed to enable the device to be cleaned with solution and/or fully submerged in cleaning solution.

In yet another embodiment, a flow through port is provided that permits solution to flow through the strip port and device to an outlet where the solution is drained out.

In some aspects of the present disclosure, a cleaning tool is provided for cleaning of a strip port of an analyte measurement device. The cleaning tool includes a handle and an end shaped like a test strip to enable the end to fit within a test strip port for cleaning.

In some aspects of the present disclosure, a strip port interface is provided to guide fluid away from the strip port opening of the strip port of the analyte measurement device.

In one embodiment, the strip port interface provides wicking capillaries via alternative paths that guide the fluid away from the strip port opening. In another embodiment, the strip port interface includes a narrow groove to guide fluid to a reservoir positioned away from the strip port opening.

In yet another embodiment, the strip port interface includes an absorbent insert that contacts or is positioned adjacent to an inserted test strip to absorb any fluid on the test strip and prevent the fluid from entering the strip port.

In some aspects of the present disclosure, absorptive elements are provided at the strip port to absorb any fluid and prevent the fluid from entering the strip port. In one embodiment, the absorptive elements couple to the strip port. In another embodiment, the absorptive elements are part of an absorptive guard that is coupled to the strip port.

In some aspects of the present disclosure, an analyte measurement device is provided that includes a gravity sensor or accelerometer to detect the orientation of the device and determine if the device is in an improper orientation to perform a control test solution. Methods related thereto are also provided.

In some aspects of the present disclosure, docking stations are provided. In one embodiment, the docking station serves as an information server for "docking" an analyte measurement device such, as a glucose meter, and also provides storage and recharging capabilities for spare batteries, such as standard batteries that can be recharged.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the present invention.

FIG. 1 illustrates a view of a measurement device including a strip connector that makes the strip interface cleanable.

FIG. 2 illustrates a perspective view of a measurement device with a strip connector.

FIG. 3 illustrates one embodiment of contacts included in a strip connector.

FIG. 4 illustrates another embodiment of contacts included in a strip connector.

FIG. 5 illustrates another embodiment of contacts included in a strip connector.

FIG. 6 illustrates a device with spring arm connectors connected with a test strip.

FIG. 7 illustrates a top view of a device with contacts that is electrically connected with a test strip.

FIG. 8 illustrates another embodiment of a device with pin contacts that interface with corresponding sockets on a test strip.

FIG. 9 illustrates a top view of pin contacts in a strip connector.

FIG. 10 illustrates a perspective view of a device that uses a disposable strip port.

FIG. 11 illustrates a side view of an end of the device including the electrical interface that receives the disposable port.

FIG. 12 illustrates a top view of a disposable port that interfaces with a device and with a test strip.

FIG. 13 is a perspective view of a disposable port that includes a separable portions such that one portion interfaces with the measurement device and another portion interfaces with a test strip.

FIG. 14 illustrates a perspective view of one embodiment of a portion of the disposable port that provides an electrical interface for a test strip.

FIG. 15 illustrates an end view of the disposable port including the test strip interface.

FIG. 16 illustrates electrical connections between the device and the test strip through the disposable port.

FIGS. 34A-34D illustrate an analyte measurement system in accordance with one embodiment presented herein.

DETAILED DESCRIPTION

Figure 17A:
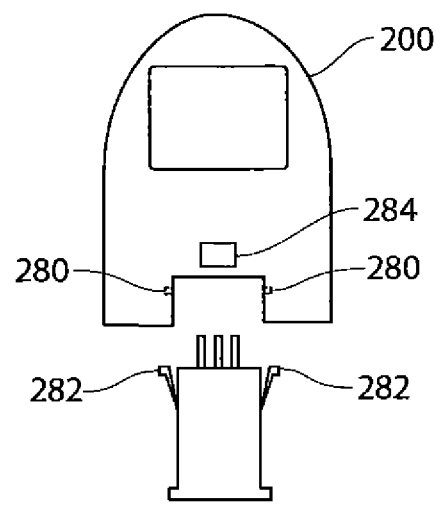
FIGS. 17A and 17B illustrate additional structure for associating the strip port with a measurement device.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The following detailed description of the figures refers to the accompanying drawings that illustrate an exemplary embodiment of an analyte measurement system. Other embodiments are possible. Modifications may be made to the embodiment described herein without departing from the spirit and scope of the present invention. Therefore, the following detailed description is not meant to be limiting.

Certain embodiments presented herein relate to electrical interfaces in measurement devices. Measurement devices often have electrical interfaces that allow them to electrically connect with another device or apparatus and perform an analysis of an analyte. A device that measures blood glucose levels, for example, includes electrical interfaces that allow the device to measure the blood glucose level from a small blood sample.

Embodiments presented herein also relate to systems and methods that can improve the mean time before failure (MTBF) in measurement devices. By improving the MTBF, a user is provided with a device that lasts longer and has more accurate performance over time.

Embodiments presented herein also relate to strip connectors or strip ports that can be cleaned and/or replaced. The ability to clean or replace a strip port can prevent the device from experiencing problems often associated with port contamination. Blood and other contaminants, for example, can often contaminate a port and make the device unusable or result in inaccurate analysis. A port that can be cleaned or replaced without affecting the operation of the device thus increases the MTBF.

One embodiment thus relates to an insert molded strip connector configuration that prevents the ingress of liquid or other contaminant. The molded strip connector can be corrosion resistant, washable, water proof, dust proof, and highly electrically conductive. In another embodiment the port, or at least a portion of the port, is disposable. A disposable port allows the device to adapt to different test strip form factors by selecting the appropriate port replacement and also allows the device to continue to function when the port is contaminated by simply replacing the contaminated port.

FIG. 1 illustrates a top view of one embodiment of a measurement device used to analyze a sample of blood. The measurement device 100 typically includes a display 102 and a user interface 104. The display 102 can be used to provide instructions or results to the user related to the measurement of the blood glucose level in a sample of blood. The user interface 104 allows a user to perform various functions, including starting the analysis, turning the device on/off, and the like.

FIGS. 1 and 2 also illustrate an example of a strip connector 110. The strip connector 110, in this example, includes a plurality of contacts 112. The contacts 112 provide a physical and/or electrical interface to an appropriately configured test strip or test strip module. In this example, the case 108 of the device 100 may be molded around the contacts 112. By molding the case 108 of the device 110 around the contacts, the interface between the case 108 and the contacts 112 becomes impervious to contamination, including liquid contamination (e.g., water, blood, etc.). The interface between the case 108 and the contacts 112 then becomes waterproof or at least sufficiently waterproof to allow the device 100, or at least the strip connector 110, to be washed. The ability to wash the device 100, or at least the strip connector 110, makes the device 100 substantially or completely corrosion resistant, washable, waterproof and dustproof. Contaminants can be removed or cleaned from the device without affecting the device 100.

The contacts 112 are usually conductive and may be gold plated to improve the conductivity of the contacts 112. The contacts 112 may also be formed of high strength steel to protect the contacts, which are exposed and extend out of the case 108 of the device 100. In other embodiments, the contacts may be formed from impregnated polymers, beryllium copper, phosphor bronze, titanium, nickel plated, tin plated or any combination thereof. In alternative embodiments, the contacts may be any material that provides the proper conductivity where necessary.

The contacts 112 can be arranged in a plurality of different configurations. The contacts can be arranged in one or more rows and/or columns on the surface 120. The contacts 112 can be arranged to connect with different sides of the printed circuit board (or other connector) inside the device 100. Further, the contacts 112 can be bent or shaped to connect with a test strip and provide the electrical and/or mechanical connection between the device 100 and the test strip. As discussed more fully herein the device 100 can be configured with various types of contacts that permit the device to interface with test strips of different form factors. In addition, other structures may extend out of the surface 120 to provide mechanical structure to secure the test strip.

FIG. 3 illustrates a side view of a device 100 including the strip port 110. In this example, the strip port 110 extends out of the device 100 through the surface 120 and the interface between the surface 120 and the contacts 112 is sealed or substantially sealed to prevent ingress of liquid or other contaminant. The contacts 112 typically pass through the surface 120 of the device 100 and include a connector 114 to the printed circuit board 106. The connector 114 may be a bond wire or other connection to form a conductive path between the printed circuit board 106 and the contacts 112. The contacts 112, in this embodiment, are pin type contacts.

FIGS. 4 and 5 illustrate additional embodiments of the contacts 112. FIG. 4 illustrates a clip pin 114 while the contact depicted in FIG. 5 is a spring arm 116. Each type of contact 112 enables physical and/or electrical contact with a corresponding test strip in a different way and may accommodate different form factors. In each example, the contacts 112 pass through the surface 120 of the device 100 and electrically connect with a printed circuit board or other circuitry inside the device. The surface 120 has been formed around the contacts 112 to provide a barrier that allows the contacts 112 to be cleaned or washed.

FIG. 6 illustrates a side view of the device 100 connected with a test strip 150. In this example, the device 100 includes spring arms 116 that extend out of the surface 120. When the strip 150 is inserted into the spring arms 116, the spring arms 116 may separate and exert a force towards the test strip 150 to hold the test strip in place physically and to provide an electrical connection between the spring arms 116 and the test strip 150. In FIG. 6, the portion 118 of the spring arms 116 inside the device 100 connect with the printed circuit board 106 on both sides in this example, although there is no requirement that each portion of each of the spring arms 116 or of the contacts in general be used to establish an electrical connection.

The case 108 of the device 100 has been formed, such as by injection molding, to form a surface 120 that encloses the portion 118 of the spring arms 116 (or other contact) inside of the device 100 while exposing the external portion of the spring arms 116 (or other contact). As a result, the interface between the spring arms 116 and the surface 120 is sealed or substantially sealed to prevent ingress of liquid such as blood or other contaminant from entering the device 100 and interfering with the operation or functionality of the device 100. As a result of this interface, the spring arms 116 or other contact can be washed or cleaned in the event of contamination or for any other reason without interfering with the operation of the device 100.

FIG. 7 illustrates a top view of the device 100 illustrated in FIG. 6. In this example, the spring arms 116 extend out of the surface 120 and are connected to the test strip 150. A blood sample 156 is loaded on the test strip and contacts 156 and 158 are in contact with the spring arms 116. In this example, the contact 158 is on one side of the test strip 150 while the contact 156 is on the other side of the test strip 150. The spring arm configuration illustrated in FIG. 7 enable contacts 158 and 156 of the test strip 150 to be on either side of the test strip. In some instances, some of the spring arms 116 may not be in electrical contact with the test strip 150.

FIG. 8 depicts a perspective view of another embodiment of a molded strip connector. In this example, the device 100 includes pin contacts 112 that pass through a surface 120 of the device 100. At least some of the pin contacts 112 encased or enclosed within the case 108 of the device 100 are electrically connected to the printed circuit board 106. Because the contact pins 112 can be arranged in various configurations, such as rows and columns, the pin contacts 112 can connect to both sides of the printed circuit board 106.

The test strip 160 illustrated in FIG. 8 includes sockets 162 that are shaped and configured to cooperate with the pin contacts 112 to establish at least an electrical connection, but may also provide physical stability to the connection between the test strip 160 and the device 100. The sockets 162 are mounted in a connection module 164 that routes the electrical connection of the sockets 162 to the strip 160 such that the device 100 can analyze any analyte located thereon.

FIG. 9 illustrates a top view a device with a test strip port. FIG. 9 illustrates that the contacts 112 can be inserted into the sockets 162 to form a connection between the device 100 and the test strip 160. When a sample is loaded in the space 166, the connection established between the device 100 and the test strip 160 via the pin contact/socket connection, the sample can be analyzed.

Another embodiment of the present disclosure relates to a disposable strip port. A disposable strip port enables the port or a portion thereof to be exchanged, by way of example and not limitation, for another port or portion thereof when the current port or portion thereof malfunctions or is contaminated. FIG. 10 illustrates a perspective view of a measurement device 200. The device 200 includes a display 202 and a user interface similar to the display and user interface illustrated in FIG. 1. The display 202 may be used to convey information including results (such as blood glucose level) on an analysis of an analyte such as a blood sample.

The device 200 includes a port 208 that is inset in a receptacle 206 formed in the device 200. The receptacle 206 can be configured to receive a disposable or replaceable port 250. As illustrated in FIG. 10, the disposable port 250 can be inserted into the receptacle 206 and connected both physically and electrically with the device 200 through the port 208. The disposable port 250 includes a strip port 252 that is configured to receive the test strip 150. When the port 250 is inserted into the receptacle 206, the surface with the port 252 is often flush with the surface 214, although other configurations are possible with respect to the position of the port 250 relative to the device 200.

FIG. 11 illustrates a view of an end of the device 200. FIG. 11 illustrates that port 208 and the printed circuit board 212 (or other suitable interface) are disposed therein at the end of the receptacle 206. The printed circuit board 212 may have traces 216 or other contacts on either side of the printed circuit board 212.

FIG. 12 illustrates a top view of the device 200, the port 250, and a test strip 150. In this example, the port 208 provides access to the contacts 216 of the printed circuit board 212. The port 250 also includes corresponding contacts 254 that are configured to connect with the traces 216. The contacts 254 may be spring arms, pins, and the like or any combination thereof. Further, the port 208 may be insert molded as previously described to provide an interface that is substantially impervious to contaminants. In this case, the port may be changeable to allow the device 200 to adapt to different form factors or to provide other functions according to the configuration of the port 250.

In this example, the port 250 also has a strip receptacle 260 (an example of the strip port 252) or strip port disposed on a side opposite the contacts 254, although the receptacle can be repositioned on any side of the port 250. The test strip 150 may be inserted into the receptacle 260 and a sample of the test strip 150 may be analyzed when the port 250 is connected to the port 208.

The port 250 in this example may include a first portion 256 and a second portion 258. The portion 256 and the portion 258 can be one integrated port or may include portions that can be repeatedly separated and connected. As previously mentioned, the portion 258 can be replace with differently configured portions to provide a receptacle 260 that accommodates different test strip form factors.

The portion 256 may be configured to interface with the device 200 via the port 208. The portion 256 may also include retention tabs 262 that interact with corresponding connectors 264 to connect at least the portion 256 with the device 200 physically. In one example, the portion 256 may permanently connect with the device 200, while allowing the portion 258 to be disposable. Advantageously, a user can select differently configured portions 258 to adapt to different configurations of the test strips. This may allow a user not only to replace the port 250 or a portion thereof, but also utilize test strips of different form factors.

FIG. 13 illustrates a perspective view of one embodiment of a disposable port 250. In this example, the port 250 includes a portion 258 that is configured to interface with test strips and a portion 253 that is configured to interface with a measurement device 200. The portion 256 includes spring arms 254 that are configured to connect with traces on a printed circuit board as previously disclosed. Alternatively, the portion 256 may include pin contacts or other contacts that interface with corresponding structure on the port 208 of the device 200 to establish the requisite connection.

The portion 256, in this example, includes a retention tab 262 that enables the port 250 to connect with the device 200 in a permanent or semi-permanent fashion. When connected to the device 200, the tab 262 keeps the portion 256 in place while the portion 258 can be separated from the portion 256 and replaced with a new portion or simply cleaned. As previously noted, the portion 258 can have multiple configurations to enable connectivity with different test strip form factors.

The port 250 includes a guide member 264, in this embodiment, that interacts with corresponding rail structure on the device 200 to facilitate insertion of the port 250 onto the device 200. The cooperation of the guide member 264 and the rail structure can ensure that the port 250 is properly aligned with the port 208 during insertion and can also prevent damage to the contacts during both insertion and/or removal of the port 250. This can prevent damage to the spring arms 254 and ensure that a proper connection is made between the port and the device.

FIG. 14 illustrates a perspective view of one embodiment of the portion 258. The portion 258 includes pins 266 that are used to connect with corresponding structure in the portion 256. The pins 266 may provide a friction fit with the corresponding structure to retain the connection between the portion 256 and the portion 258.

FIG. 15 illustrates a view of a test port or receptacle 260 of the portion 258. In this example, the portion 258 includes a receptacle 260 configured to receive a test strip. Contacts 270 are disposed inside the port and arranged to make at least electrical contact with the test strip in order to allow analysis of the blood sample on the strip.

FIG. 16 depicts a side view the device 200 with a disposable port 250 connected thereto. FIG. 16 illustrates the spring arms 264 inside of the portion 256. On the device side, the spring arms extend out of the port 250 and make contact with the printed circuit board 212 inside the device 200. The opposite end of the spring arms 264 form sockets 272. The sockets 272 are configured to receive and electrically connect with the pins 266 that extend out of the portion 258. The pins 266 also include contacts 270 (illustrated as spring arms in this example) inside of the portion 258 that are configured to electrically connect with a test strip 150 when the test strip inserted in the receptacle or port 260.

As previously stated, the portion 258 can be configured to adapt to multiple strip form factors. As a result, the portion 258 may also include contacts 270 that are configured as pins, plugs, sockets, clips, and the like or any combination thereof. The interface between the portion 256 and 258 allows at least the portion 256 to be replaceable whenever it begins to fail or is contaminated or for any other reason. Further, the electrical connections between the device 200, the portion 256, the portion 258, and the test strip 150 can take various forms including, but not limited to, pin contacts, clip pins, spring arms, and the like or any combination thereof. In this example, the contacts or pins illustrated for the portions 256 and 258 cooperate to establish electrical connections.

Figure 17B:
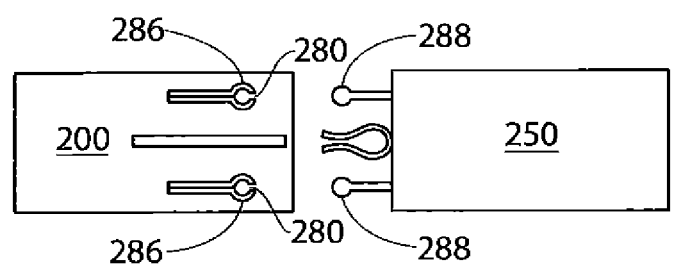

FIGS. 17A-B illustrates examples of the connections or associations between the port 250 and the device 200. FIG. 17A illustrates that the connection between the port and the device may include a latch 282 that interfaces with a receptacle 280 to secure the portion 256 to the device 200. The receptacle 280 and latch 282 cooperate to provide a connection. A release 284 may also be included in the device 200 that releases the latch 282 from the receptacle 280. As a result, the connection illustrated in FIG. 17A can be permanent or semi-permanent.

FIG. 17B illustrates another interface or connection between the device 200 and the port 250. In this example, the device may include sockets 286 that have an opening adapted to receive the ball 288 connected to the port 250. The ball 288, when snapped into the socket 286, expands the socket 286 to allow the ball 288 to enter the socket 286. Once the ball is inserted, the socket contracts to establish the connection. As a result, a force is required to insert the ball 288 into the socket. A similar force may be required to release the connection illustrated in FIG. 17B. In these examples, the connection may be semi-permanent and ensures that the electrical connection is maintained.

In other embodiments, the connection between the port 250 and the device 200 (or between the contact pins 266 and sockets 272) may include a press fit or a friction fit. For instance, the port 250 may be slightly wider than the receptacle 206. As the port 250 is inserted into the receptacle 206, the friction between the port 250 and the device 200 maintains the port in the proper position.

In other embodiments, the electrical connections can also provide the mechanical connection. For example, a friction fit between the pins 266 and the sockets 272 may provide sufficient force to keep the portions 256 and 258 connected. A user, however, can remove the portion 256 and replace it.

Figure 18:
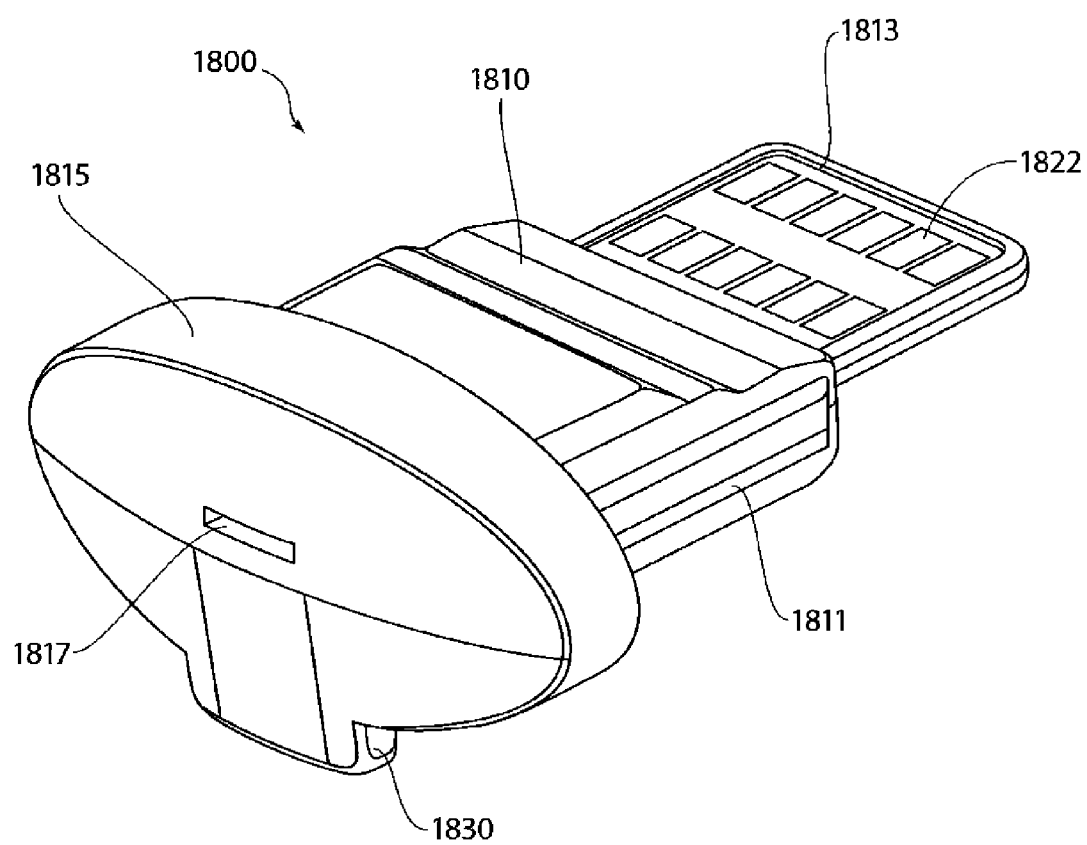
FIG. 18 is a front-side perspective view of a replaceable strip port module in accordance with one embodiment presented herein.
Figure 19:
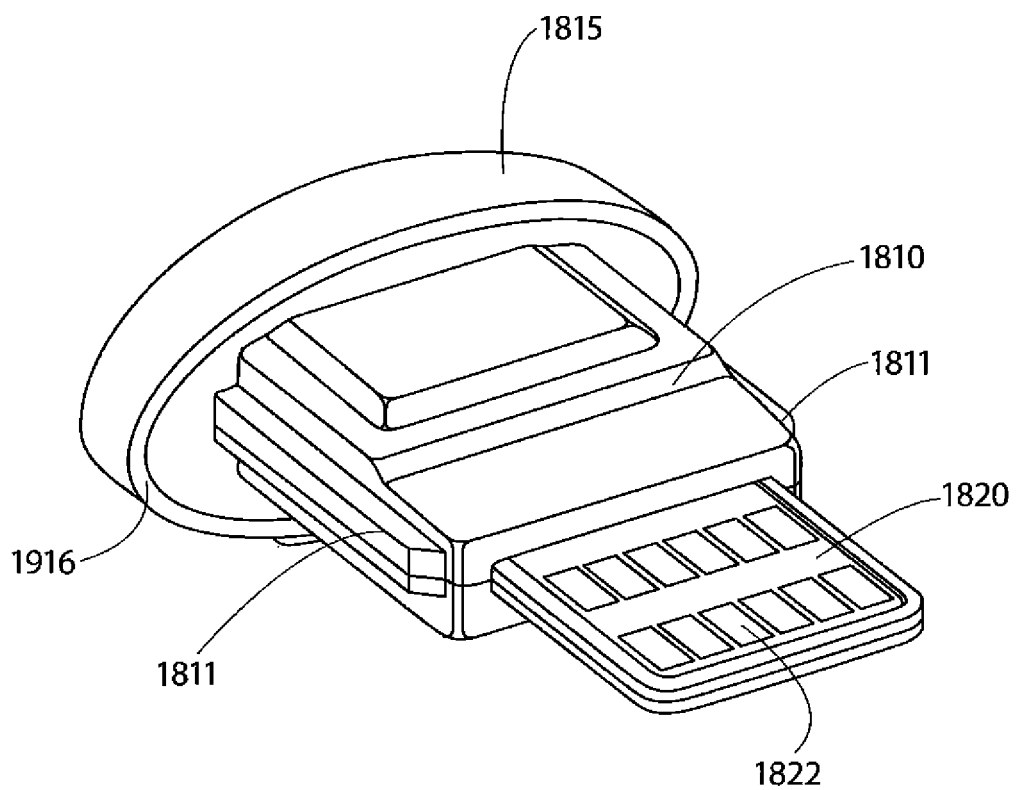
FIG. 19 is a back-side perspective view of the replaceable strip port module of FIG. 18.
Figure 20:
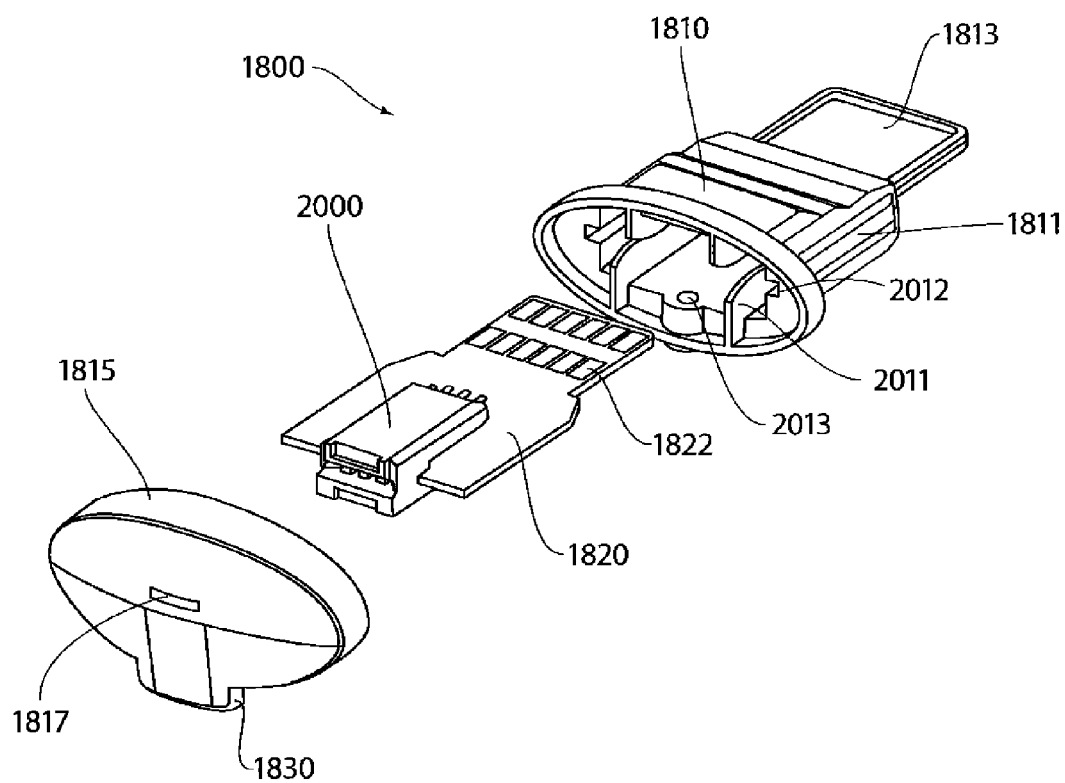
FIG. 20 is an exploded view of the replaceable strip port module of FIG. 18, showing the internal components of the replaceable strip port module.
Figure 21:
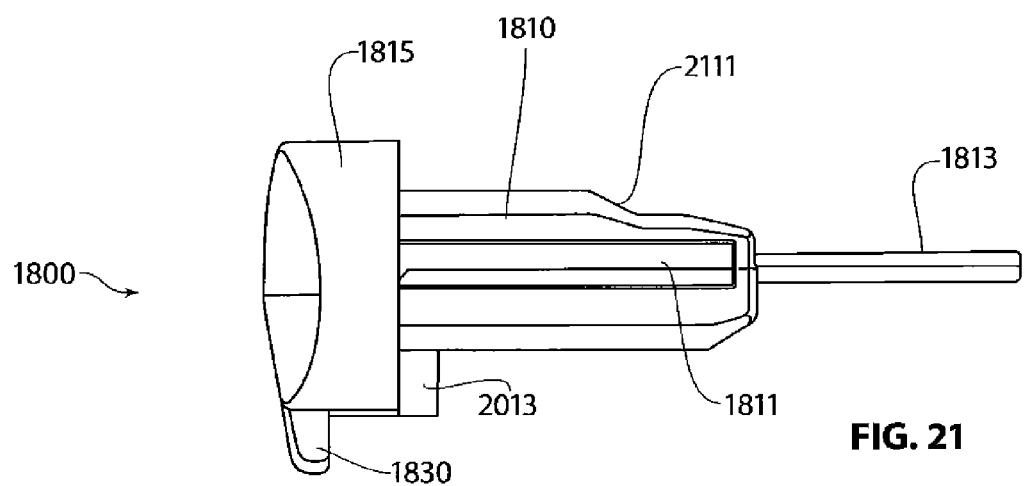
FIG. 21 is a side view of the replaceable strip port module of FIG. 18.
Figure 22:
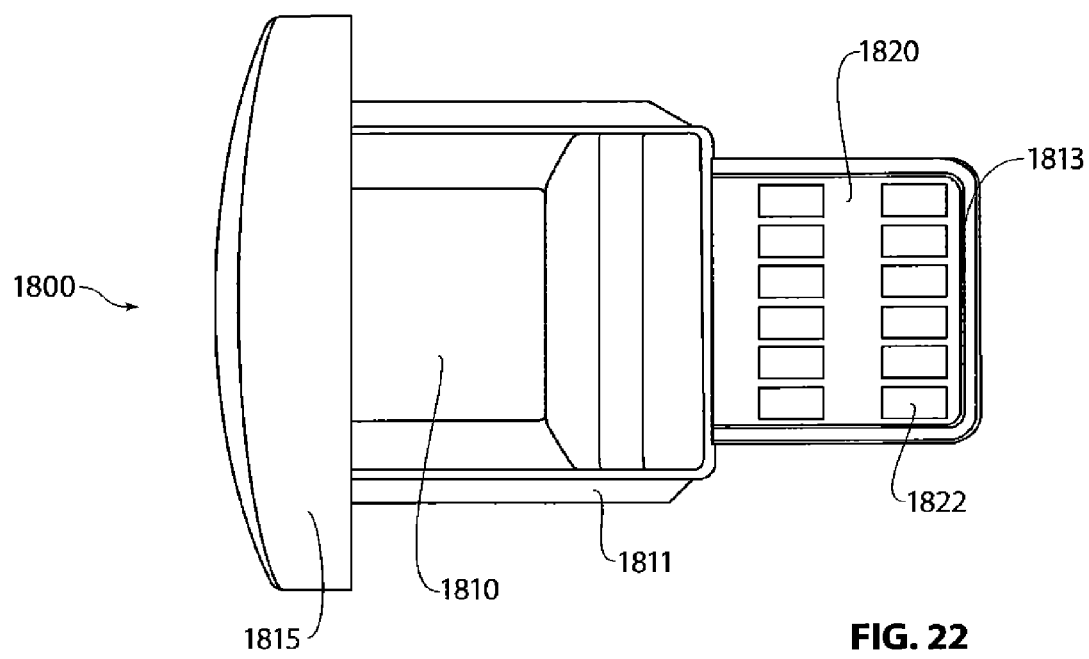
FIG. 22 is a plan view of the replaceable strip port module of FIG. 18.

FIGS. 18-22 provide various views of a replaceable strip port module 1800, in accordance with another embodiment presented herein. For example, FIG. 18 is a front-side perspective view of replaceable strip port module 1800. FIG. 19 is a back-side perspective view of replaceable strip port module 1800. FIG. 20 is an exploded view of replaceable strip port module 1800. FIG. 21 is a side view of replaceable strip port module 1800. FIG. 22 is a plan view of replaceable strip port module 1800.

As shown in FIGS. 18-22, replaceable strip port module 1800 includes a housing 1810 with a cap 1815. An analyte test strip port 2000 is disposed within an open end of housing 1810, which is then enclosed (or covered) by cap 1815. In one embodiment, analyte test strip port 2000 is an electro-chemical strip port. In an alternative embodiment, analyte test strip port 2000 is an optical strip port. As shown in FIG. 20, analyte test strip port 2000 is coupled to a printed circuit board (PCB) 1820, and electrical leads of analyte test strip port 2000 are electrically coupled to one or more contact pads 1822 on PCB 1820. Housing 1810 includes an interface portion (or interface aperture) 1813 to expose contact pads 1822 when analyte test strip port 2000 and PCB 1820 are inserted and aligned within housing 1810. In one embodiment, a seal member may be provided along the edge of interface aperture 1813 to provide a fluid tight seal between PCB 1820 and housing 1810.

In one embodiment, housing 1810 is formed of a plastic mold, and more preferably an anti-microbial plastic mold. In alternative embodiments, housing 1810 may be formed of other suitable materials such as rubbers, polymers, or thermally conductive materials. In one embodiment, for example, housing 1810 and internal components is formed of medical grade PC/ABS plastic blend, and may include an anti-microbial plastic such as BAYER BAYBLEND AM120FR. In the embodiment shown in FIG. 20, housing 1810 includes internal alignment features, such as internal alignment baffles 2011 and internal alignment grooves 2012, to properly align analyte test strip port 2000 and PCB 1820 within housing 1810. Such internal alignment features, and structures equivalent thereto, serve as means for aligning an analyte test strip port within the module housing. A screw hole 2013 is provided in housing 1810 to attach replaceable strip port module 1800 to an analyte meter, as further discussed below. A screw for use in screw hole 2013 may be a stainless steel, pan head Philips, thread-forming screw.

Housing 1810 also includes external alignment features or guides 1811 and beveled surfaces 2111 to further support the proper insertion and alignment of replaceable strip port module 1800 within an analyte meter. Such external alignment features, and structures equivalent thereto, serve as means for aligning a replaceable strip port module within an analyte meter.

Cap 1815 serves to fully encase analyte test strip port 2000 within housing 1810. In one embodiment, cap 1815 is permanently attached to housing 1810 with a hermetic seal 1916. In an alternative embodiment, cap 1815 may be removably attached to housing 1810. In another alternative embodiment, a gasket means (e.g., a rubber o-ring, fabric, etc.) may be used to seal the gap between cap 1815 and housing 1810. In the embodiment shown, cap 1815 also includes an optional tab extension 1830 to facilitate in the insertion and removal of replaceable strip port module 1800 from an analyte meter.

Cap 1815 further includes an aperture 1817, which provides access to analyte test strip port 2000. In operation, an analyte test strip is inserted through aperture 1817 and into analyte test strip port 2000. In one embodiment, aperture 1817 provides sufficient clearance to accept a wide variety of different analyte test strips form factors. In an alternative embodiment, aperture 1817 may be customized to receive a specific analyte test strip form factor. Customizing the aperture size or shape to a specific analyte test strip form factor can prevent the use of non-matching or incompatible analyte test strips with analyte test strip port 2000. Aperture 1817 may also be formed with a one-way valve or port protector to swipe across the surface of an analyte test strip when the analyte test strip is passed through aperture 1817. Such an embodiment may be used to protect analyte test strip port 2000 from unwanted contaminants. In alternative embodiments, aperture 1817 may incorporate one or more port protectors, such as disclosed in U.S. Patent Application Publication No. 2009/0270696, which is incorporated by reference herein in its entirety.

Figure 23:
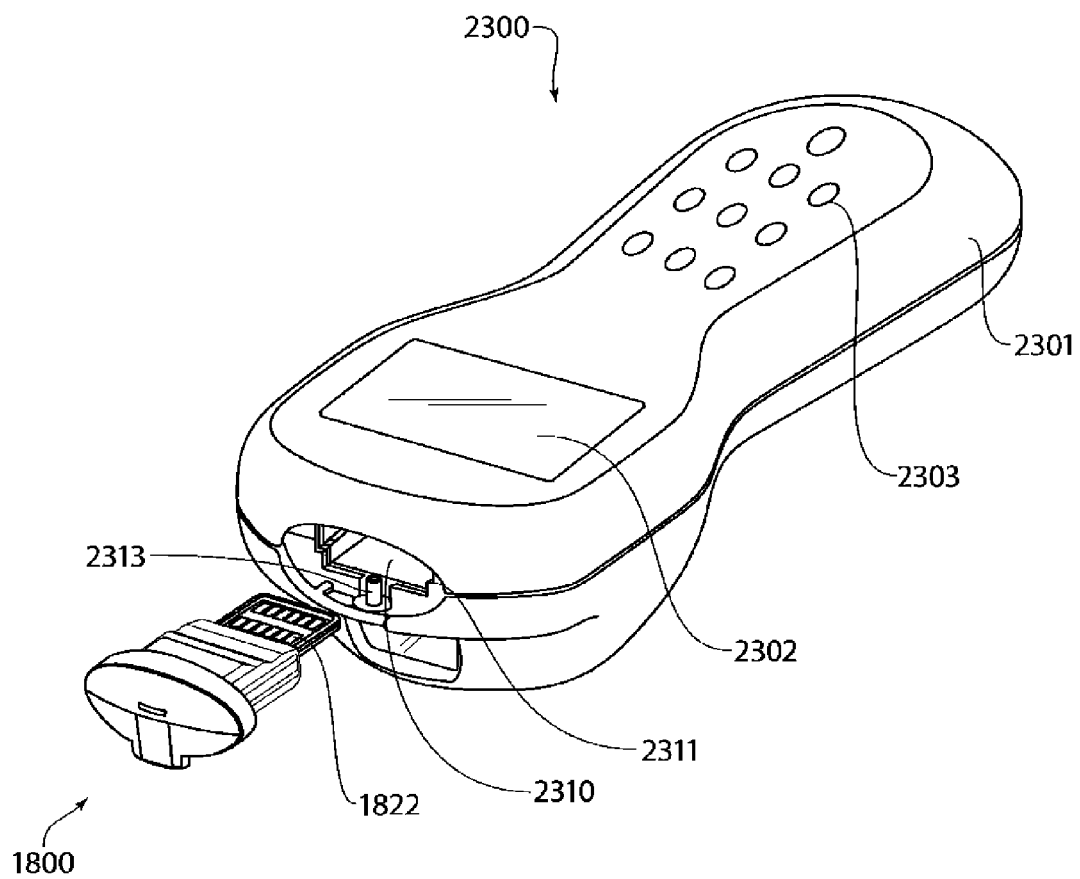
FIG. 23 is a perspective view of a modular analyte measurement system in accordance with one embodiment presented herein.
Figure 24:
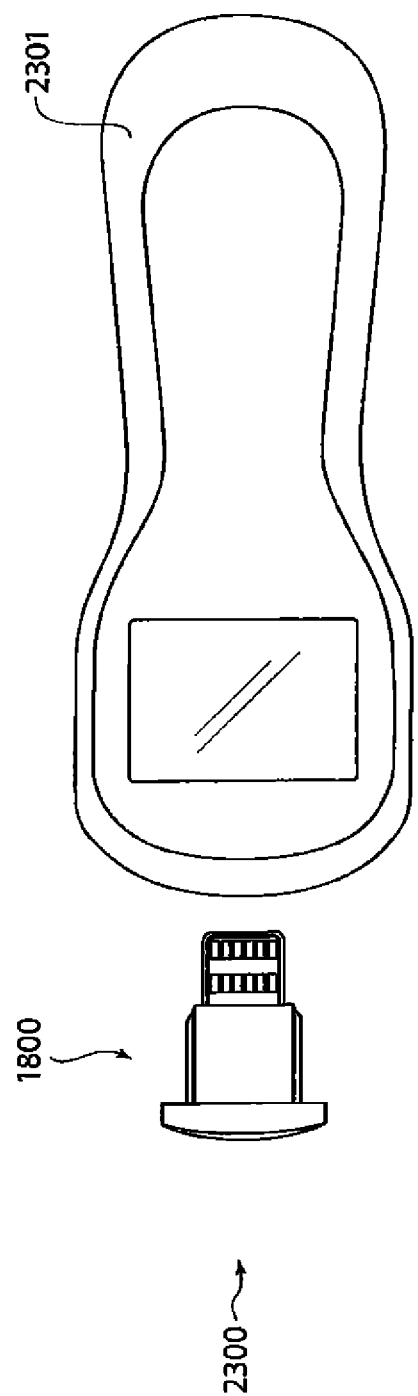
FIG. 24 is a plan view of the embodiment shown in FIG. 23.
Figure 25:
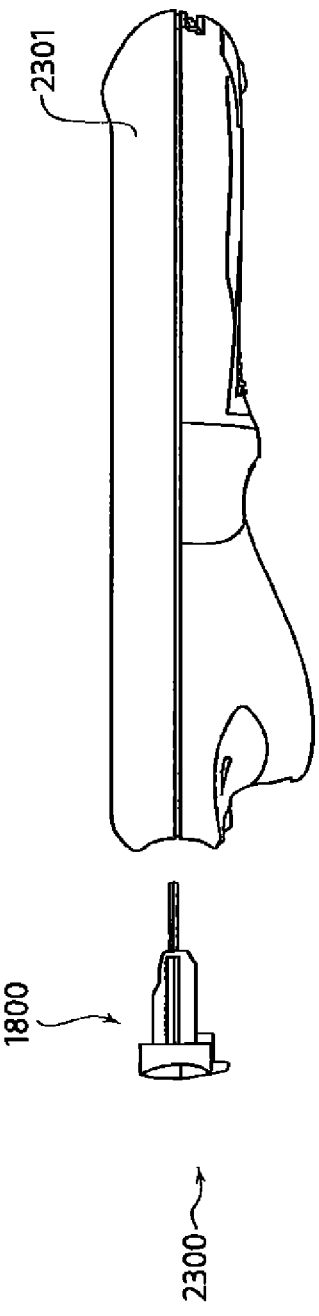
FIG. 25 is a side view of the embodiment shown in FIG. 23.
Figure 26:
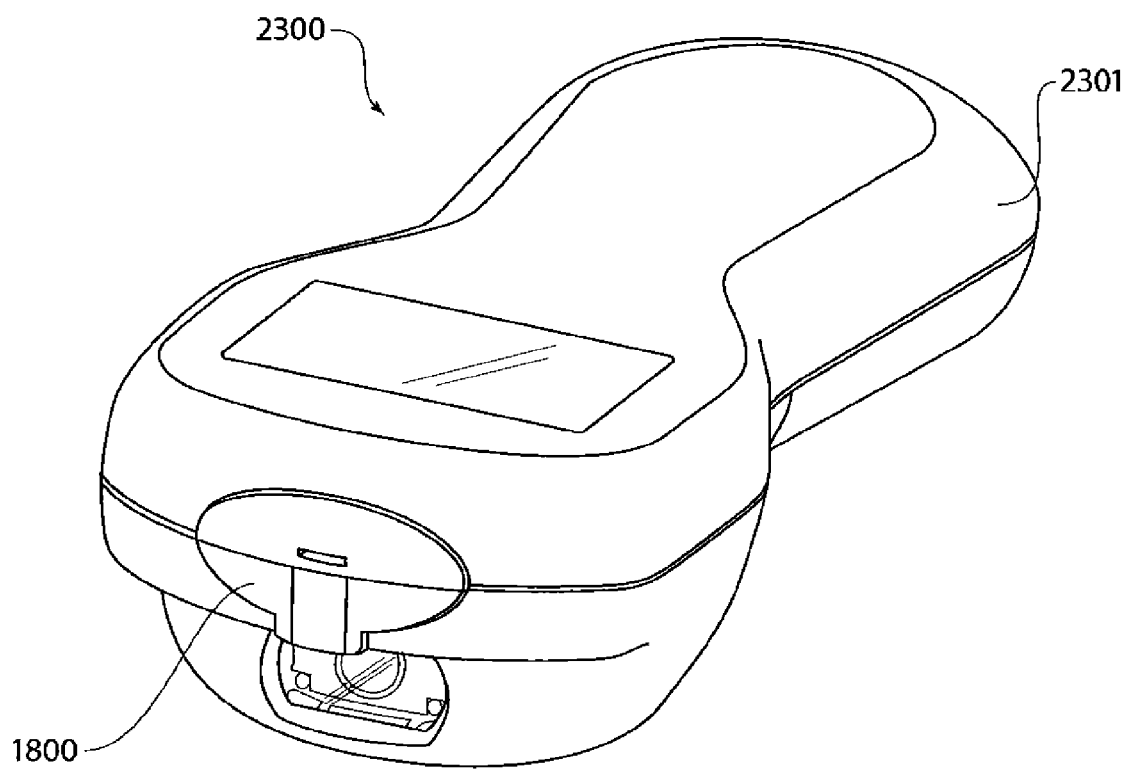
FIG. 26 is a view of the embodiment shown in FIG. 23, having the replaceable strip port module inserted into the analyte meter.
Figure 27:
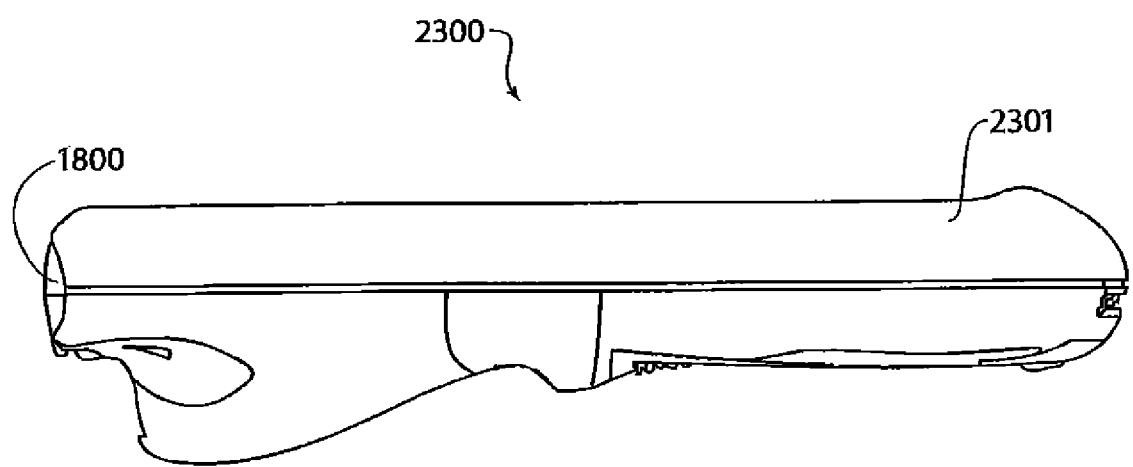
FIG. 27 is a side view of the embodiment shown in FIG. 26.
Figure 28:
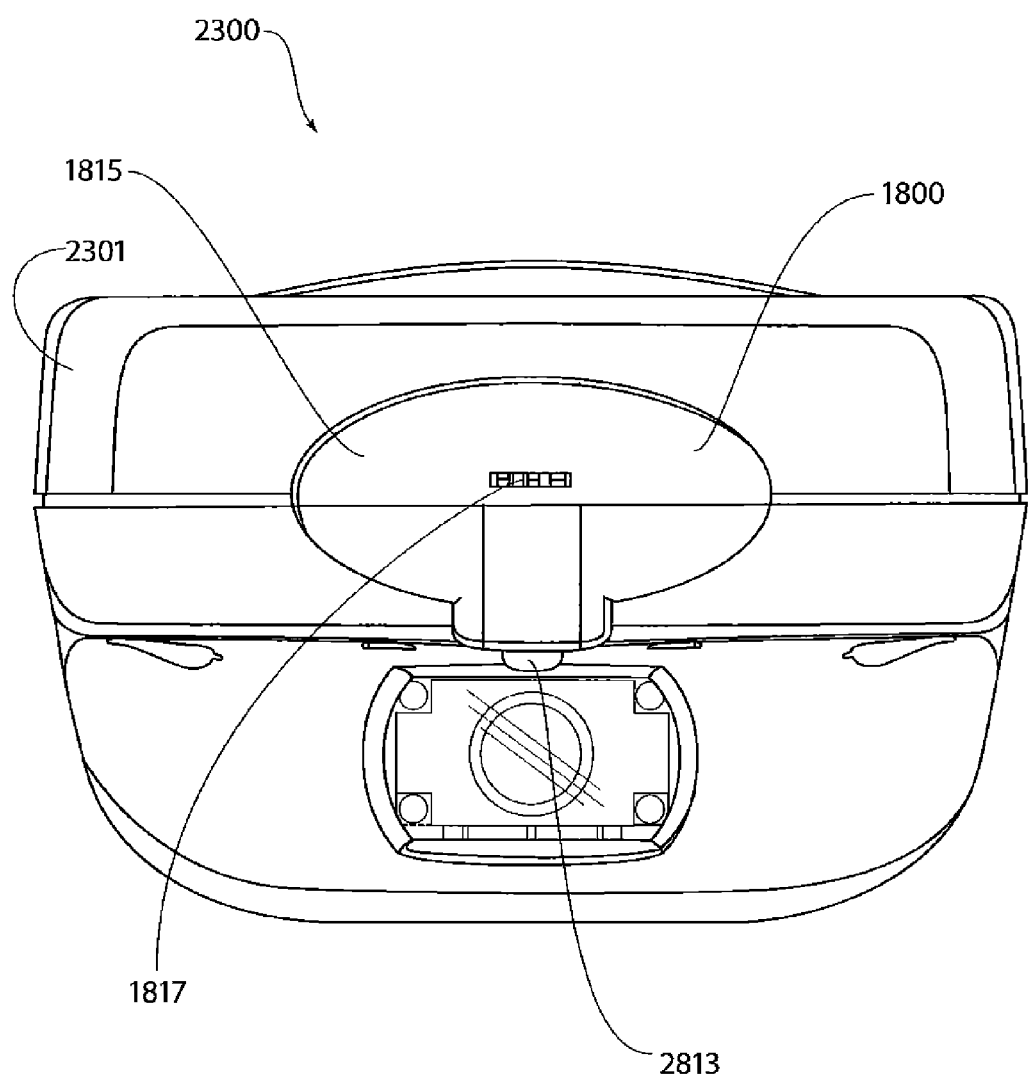
FIG. 28 is a front-side view of the embodiment shown in FIG. 26.
Figure 29A:
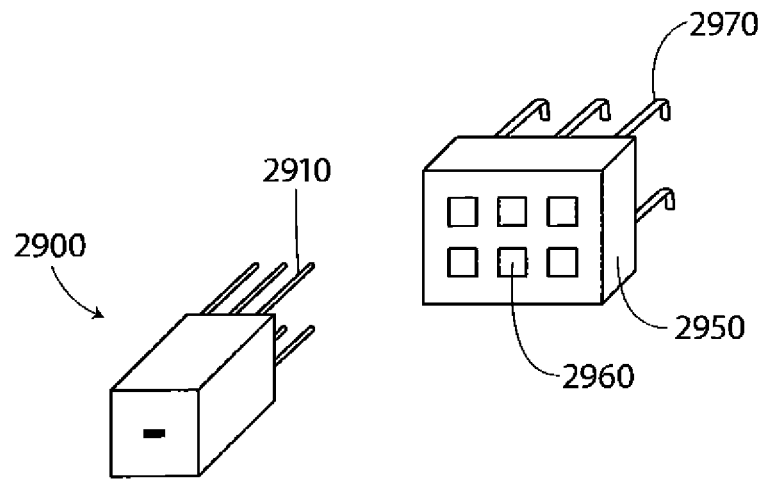
FIGS. 29A and 29B illustrate perspective and side views, respectively, of a pin-header connector form.
Figure 29B:
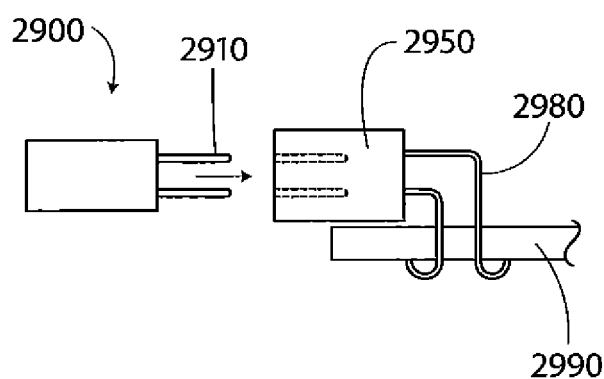

FIGS. 23-28 illustrate a modular analyte measurement system 2300, including a replaceable strip port module, such as replaceable strip port module 1800, and an analyte meter 2301. For example, FIGS. 23-25 are perspective, plan, and side views, respectively, of system 2300 prior to insertion of replaceable strip port module 1800 into analyte meter 2301. FIGS. 26-28 are perspective, side, and front views, respectively, of system 2300 having replaceable strip port module 1800 inserted into analyte meter 2301.

Analyte meter 2301 may be similar to analyte meters known in the art. For example, analyte meter 2301 may include similar structures, functions, and components as the analyte meters described in U.S. Pat. No. 7,077,328, which is incorporated herein by reference in its entirety. As shown, analyte meter 2301 includes a display panel 2302 for displaying instructions and/or results from an analyte measurement, and a user interface 2303 (not shown in FIGS. 24-28) for inputting commands to the analyte meter. Analyte meter 2301 also includes internal processing units (not shown) for the analysis of a blood sample. As such, analyte meter 2301 includes means for analyzing an electrical signal received from an analyte strip port. Analyte meter 2301, however, has been modified to lack a fully integrated analyte test strip port. Instead, analyte meter 2301 provides an open electrical interface with electrical contacts corresponding to the electrical contacts of a typical analyte test strip port. Such open electrical interface couples with the exposed contact pads 1822 of replaceable strip port module 1800 to complete analyte measurement system 2300.

For example, as shown in FIG. 23, analyte meter 2301 includes a receptacle 2310 that provides an opening in the analyte meter housing. Replaceable strip port module 1800 is designed to fit within receptacle 2310. Guide features 2311 are provided in the meter housing to aide in the insertion and alignment of replaceable strip port module 1800 within receptacle 2310. Analyte meter 2301 also includes a screw hole 2313, which aligns with screw hole 2013 in replaceable strip port module 1800. As such, replaceable strip port module 1800 can be removably attached to analyte meter 2301 with a screw 2813 (see FIG. 28). Alternative attachment means may also be employed to removably (or semi-permanently) attach replaceable strip port module 1800 to analyte meter 2301. Screw holes 2013 and 2313, and screw 2813, as well as equivalent structures, thereby serve as means for removably attaching the replaceable strip port module to the analyte meter. In one embodiment, for example, the meter housing and internal components is formed of medical grade PC/ABS plastic blend, and may include an anti-microbial plastic such as BAYER BAYBLEND AM120FR. In one embodiment, meter housing is formed of two or more separate components, which are screwed together using M3 stainless steel screws. Such screws may have heads that differentiate them from the strip port retaining screws. For example, such screws may have Torx heads. Internal screws may be M2.5 zinc-plated, pan head Philips screws.

In operation, contact pads 1822 couple to corresponding open electrical connections (not shown) inside of analyte meter 2301. In one embodiment, the open electrical connections are SIM connections that are electrically coupled to a PCB within analyte meter 2301. In one embodiment, any or all contact pads 1822 or connectors include gold or gold-plating. As such, electrical communication can be provided between analyte test strip port 2000 and analyte meter 2301. In alternative embodiments, the connection between replaceable strip port module 1800 and analyte meter 2301 may be in the form of edge connectors, pin headers, compression connectors, or other equivalent connectors. Such connector forms, and structure equivalent thereto, serve as an electrical interface or means for electrically coupling the analyte test strip port to the analyte meter.

FIGS. 29-32 illustrate alternative connector forms. FIGS. 29A and 29B, for example, illustrate perspective and side views, respectively, of a pin-header connector form. In the embodiment shown, a replaceable strip port module 2900 is electrically coupled to a header 2950 in an analyte meter. Pins 2910, which are electrically coupled to leads in an analyte test strip port within replaceable strip port module 2900, are configured to mate with header ports 2960. Electrical current can then flow from header 2950 to PCB 2990 through contacts 2970.

Figure 30:
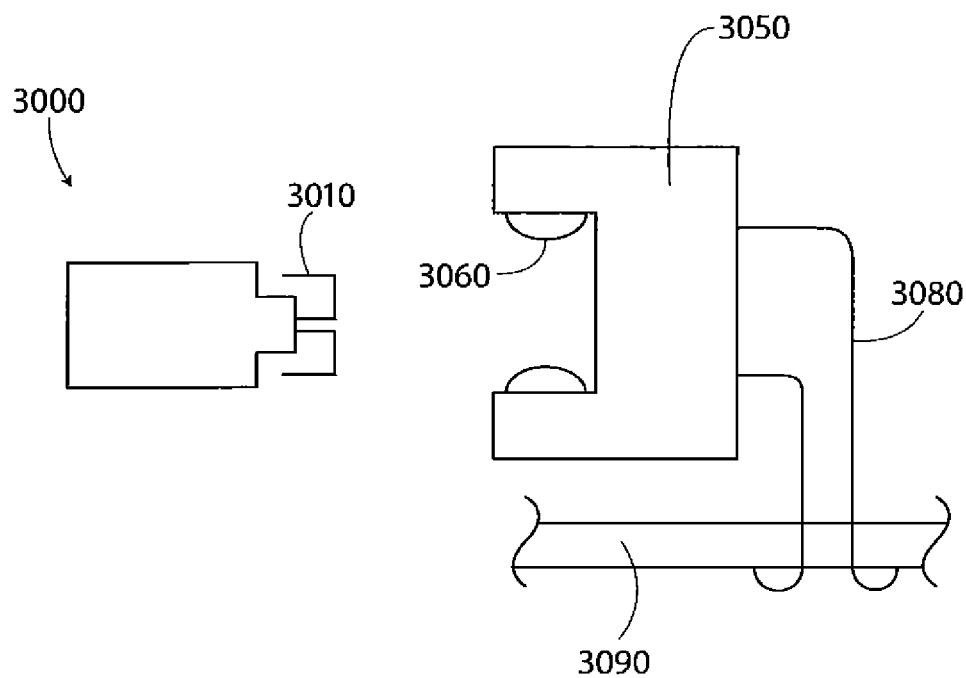
FIG. 30 illustrates a side views of an edge connector form.

FIG. 30 illustrates a side views of an edge connector form. In the embodiment shown, a replaceable strip port module 3000 is electrically coupled to an edge connector 3050 in an analyte meter. Pins 3010, which are electrically coupled to leads in an analyte test strip port within replaceable strip port module 3000, are tail-wrapped and configured to mate with edge connector input contacts 3060. Electrical current can then flow from edge connector 3050 to PCB 3090 through contacts 3070.

Figure 31:
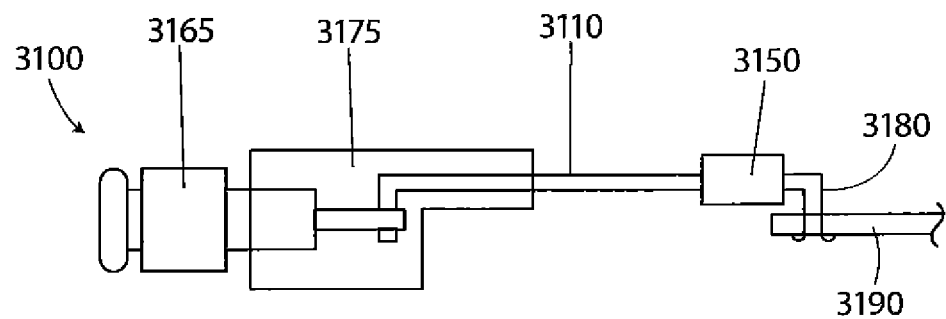
FIG. 31 illustrates a side views of an alternative connector form.

FIG. 31 illustrates a side views of an alternative connector form. In the embodiment shown, a replaceable strip port module 3100 is electrically coupled to a connector 3150 in an analyte meter. A soldered wire 3110 is used to electrically couple leads in an analyte test strip port within replaceable strip port module 3100 to connector 3150. A heat sink 3175 is used for thermal control of wire 3110. Electrical current can then flow from connector 3150 to PCB 3190 through contacts 3170. A rubber gasket 3165 is used to align and replaceable strip port module 3100 to the meter housing.

Figure 32:
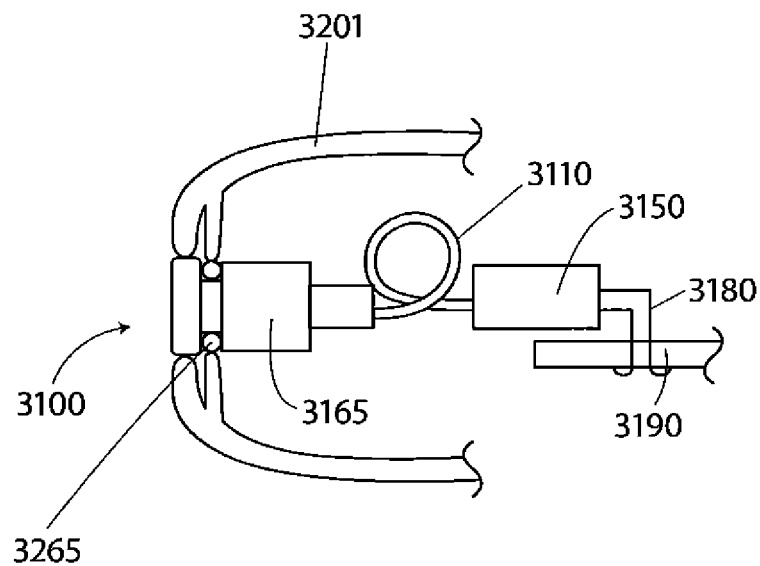
FIG. 32 illustrates the replaceable strip port module of FIG. 31.

FIG. 32 illustrates the replaceable strip port module 3100 of FIG. 31, installed within a meter housing 3201. As shown in FIG. 32, rubber gasket 3165 aligns and maintains replaceable strip port module 3100 in place. A rubber gasket 3265 is also employed to further align and maintain replaceable strip port module 3100 in place. As shown in FIG. 32, wire 3110 is looped during installation. Wire 3110 is provided with such additional length to provide flexibility and functionality to the system. In the event that a user wishes to perform an analyte test at a distance from the meter, replaceable strip port module 3100 may be withdrawn from housing 3201 and an analyte test may be performed while the module and meter remain connected through wire 3110.

A common analyte strip port requires three functional leads for connection with a meter. In the embodiment shown in FIGS. 18-28, analyte test strip port 2000 provides a line-for-line connection with three of the twelve contact pads 1822. The additional nine contact pads of replaceable strip port module 1800 allow for customization of system 2300. For example, in one embodiment, a replaceable strip port module having a glucose test strip port may be used to measure the user's glucose levels. Such embodiment could employ contact pads 1, 2, and 3, as functional contacts, and contact pads 4 and 5 as identification leads to identify the module to the meter as a glucose module. The replaceable strip port module with the glucose test strip port may then be replaced with a replaceable strip port module having a ketone test strip port to measure the user's ketone levels. Such a ketone module may use contact pads 6, 7, and 8, as functional contacts, and contact pads 9 and 10 as identification leads to identify the module to the meter as a ketone module. Such customization adds to the functionality of system 2300.

In the event that unwanted fluids and contaminants enter through aperture 1817 and comprise the function of analyte test strip port 2000, replaceable strip port module 1800 can be removed and replaced with a new replaceable strip port module. The replacement of replaceable strip port module 1800 can be done without discarding or replacing any of the functioning components of analyte meter 2301. As such, a user/manufacturer can save money by only replacing the components of the system 2300 that have actually been comprised.

Figure 33:
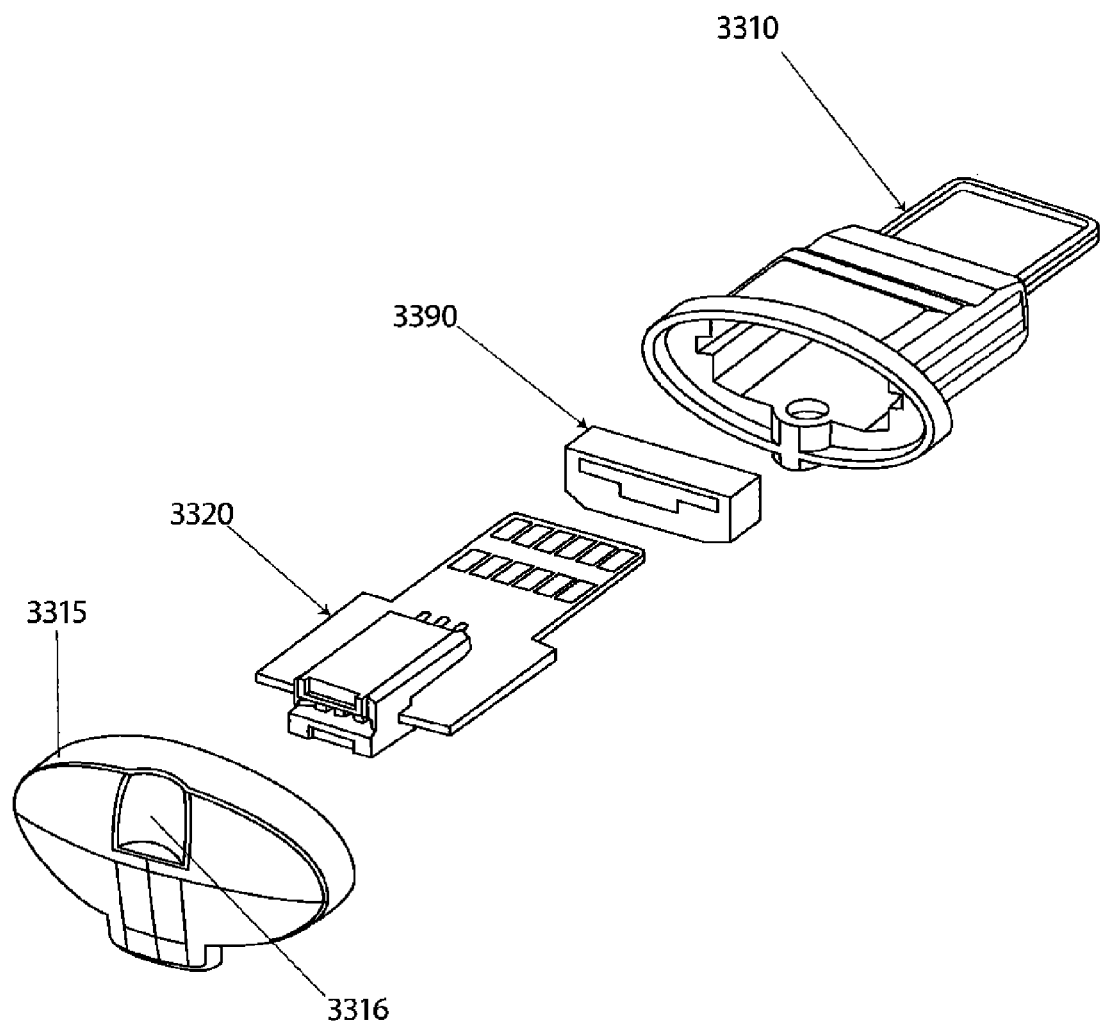
FIG. 33 is an exploded view of a replaceable strip port module, in accordance with another embodiment presented herein.
Figure 35A:
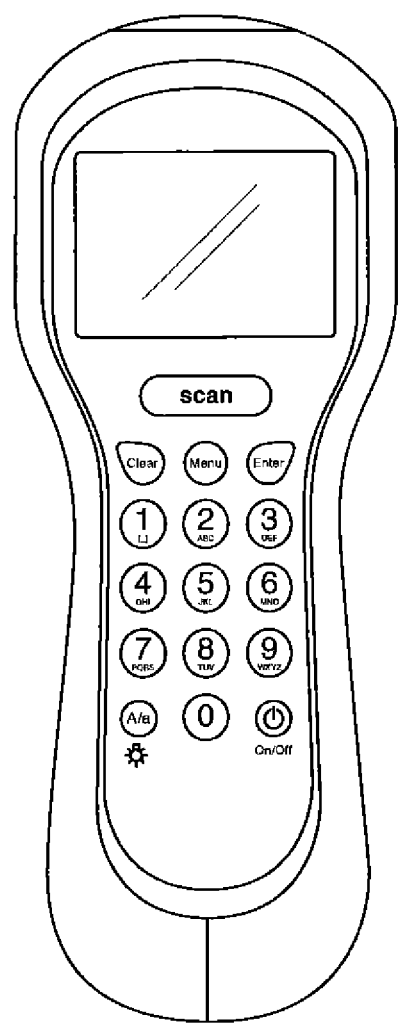
FIGS. 35A-35D illustrate an analyte measurement system in accordance with another embodiment presented herein.
Figure 35B:
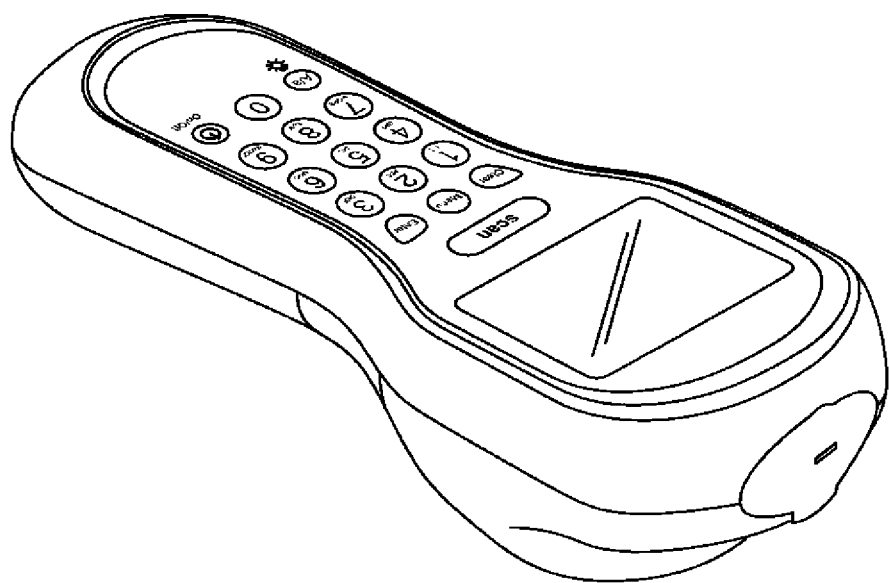
Figure 35C:
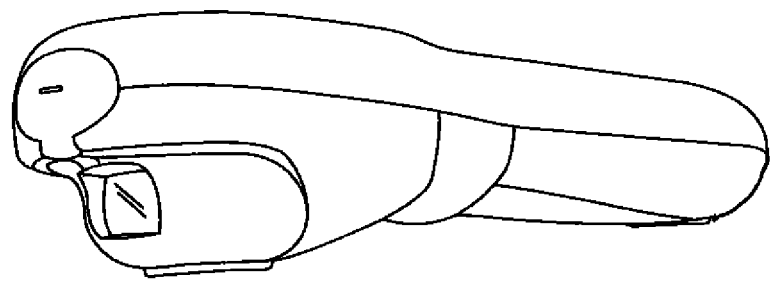
Figure 35D:
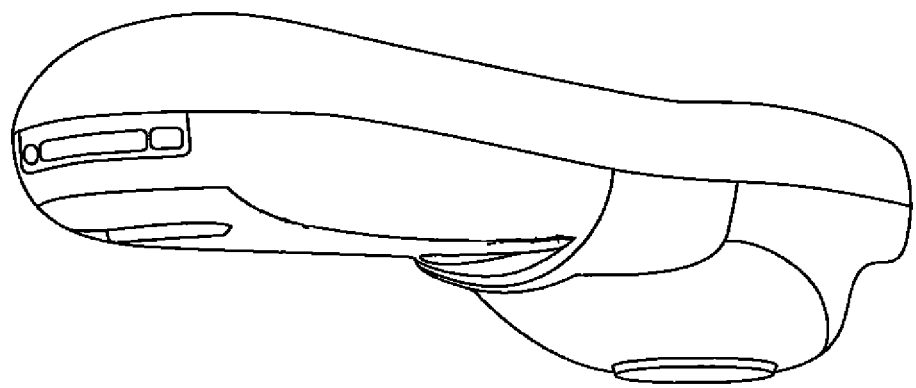

FIG. 33 is an exploded view of a replaceable strip port module, in accordance with another embodiment presented herein. The replaceable strip port module of FIG. 33 is similar to the replaceable strip port module 1800 of FIG. 20, and includes a housing 3310, PCB 3320 with respective strip port, and cap 3315. However, the replaceable strip port module of FIG. 33 also includes a gasket 3390. Further, cap 3315 differs from cap 1815 in that cap 3315 includes an indented region 3316 on a surface of the cap, which may facilitate entry and/or alignment of a test strip therein.

In operation, gasket 3390 sits within housing 3310 and serves as a holder, alignment element, and/or seal for PCB 3320. For example, gasket 3390 may be sized to provide a fluid tight seal around PCB 3320. Gasket 3390 may also be sized and configured to swipe across a surface of PCB 3320 so as to clean a surface of PCB 3320 when the PCB is inserted through the gasket. Gasket 3390 may also be sized to provide a press-fit engagement with the interior surfaces of housing 3310.

In one embodiment, a cap gasket (not shown) is provided as a seal between cap 3315 and the meter housing. Further, a second cap gasket (not shown) may be provided as a seal between cap 3315 and strip port module housing 3310. In yet another embodiment, a single cap gasket (not shown) may be provided as a seal between cap 3315 and strip port module housing 3310 and the meter housing.

FIGS. 34A-34D illustrate an analyte measurement system in accordance with one embodiment presented herein. The views presented in FIGS. 34A-34D show the ornamental designs of an analyte measurement system embodiment.

FIGS. 35A-35D illustrate an analyte measurement system in accordance with yet another embodiment presented herein. The views presented in FIGS. 34A-34D show the ornamental designs of another analyte measurement system embodiment.

Figure 36A:
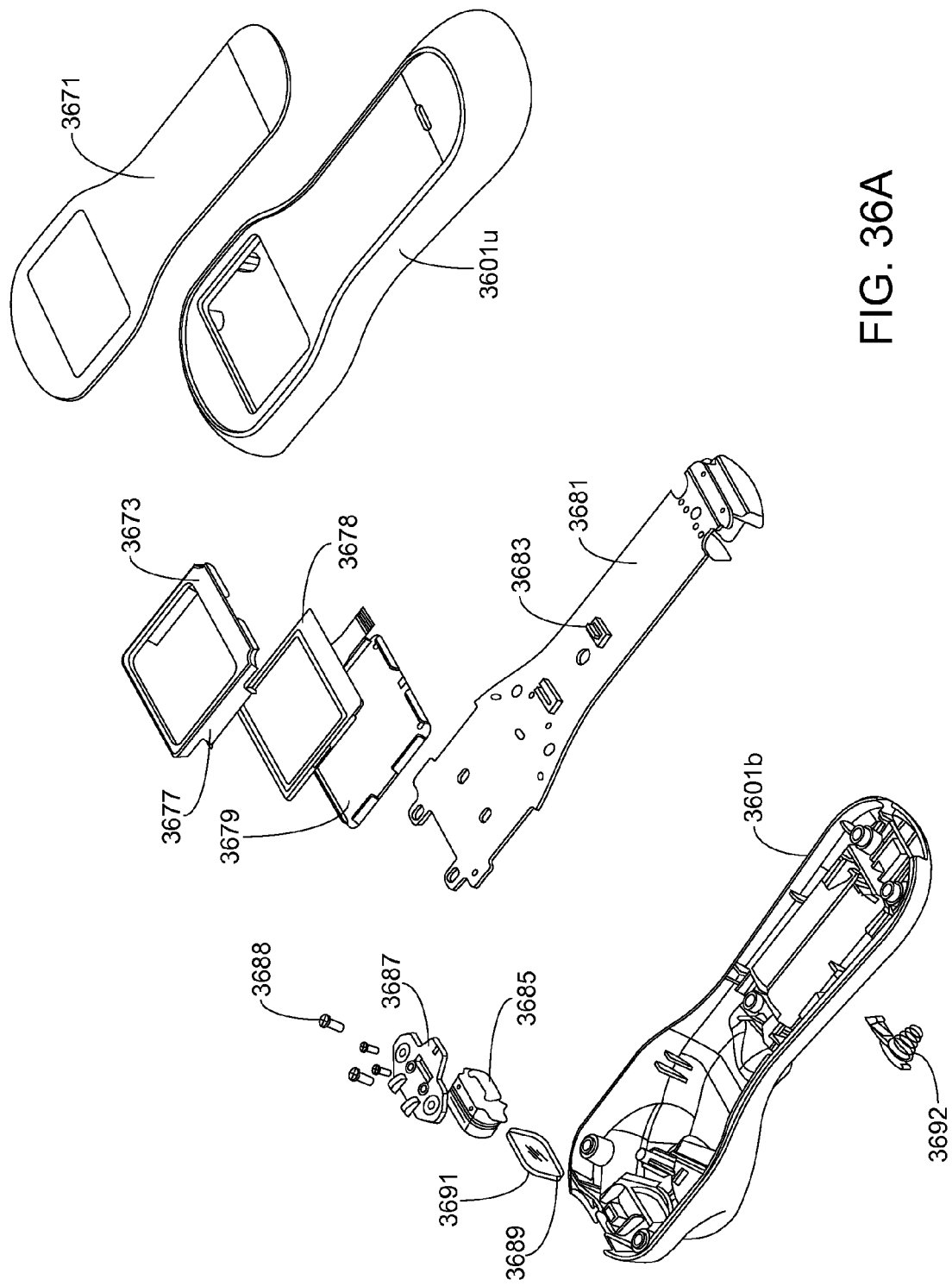
FIGS. 36A-36D are assembly drawings of an analyte measurement system in accordance with an embodiment presented herein.

FIGS. 36A-36D are assembly drawings of an analyte measurement system in accordance with an embodiment presented herein. As shown in FIG. 36A the analyte measurement system includes an upper housing component 3601U and a bottom housing component 3601B. A membrane 3671 is laid over upper housing component 3601U. In one embodiment, membrane 3671 includes an anti-microbial layer. Membrane 3671 may also include electrical contacts that serve as buttons.

Figure 36C:
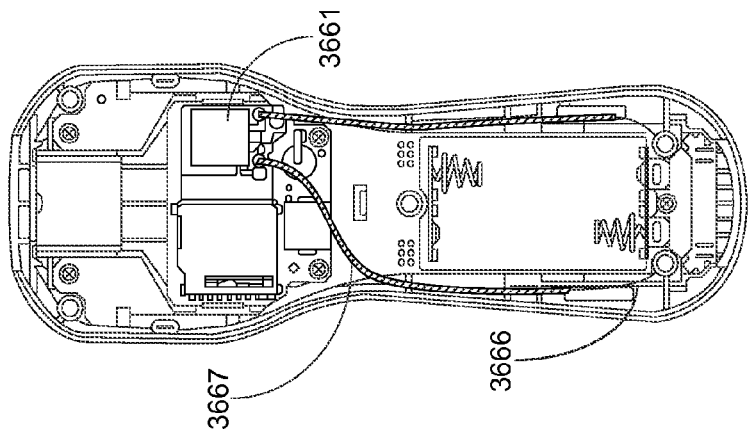
Figure 36B:
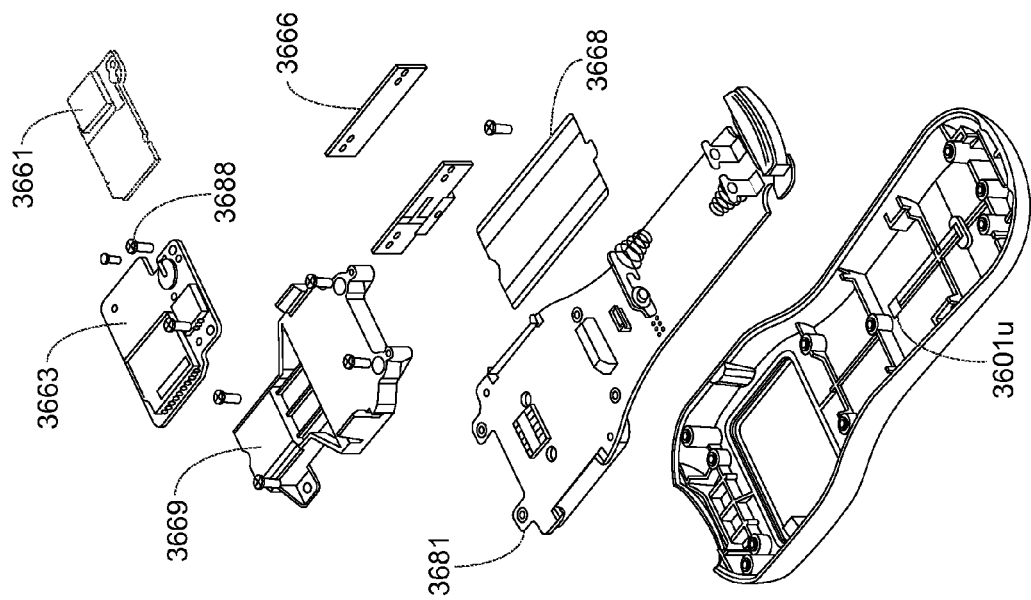

An LCD assembly 3681 is provided on a PCB 3683. LCD assembly 3681 includes an LCD frame 3673. Deformable frame tabs 3677 are provided on LCD frame 3673 to engage with the underside of PCB 3683. As such, LCD frame 3673 is grounded to PCB 3683. LCD assembly 3681 further includes an LCD screen (and associated circuitry) 3678 and backlight 3679. LCD assembly 3681 is mounted to upper housing component 3601U, as shown in FIGS. 36B and 36C.

Mounted on bottom housing component 3601B is a barcoding system including scanner 3685 and lens 3691. Scanner 3685 is coupled to bottom housing component 3601B with mounting plate 3687 and screws 3688. The barcoding system may include a 2D or 3D scanner, and may be used to identify a patient, test strip, and/or healthcare provider.

On the underside of LCD assembly 3681 in a communications module including a WiFi module 3661 mounted on a WiFi PCB 3663. WiFi PCB 3663 is then coupled to carriage 3669, which is then attached to LCD assembly 3681. Wires 3667 connect WiFi module 3661 to antennae 3666, which sit on the side of upper housing component 3601U. A shield 3668 is then attached to the underside of LCD assembly 3681.

Figure 36D:
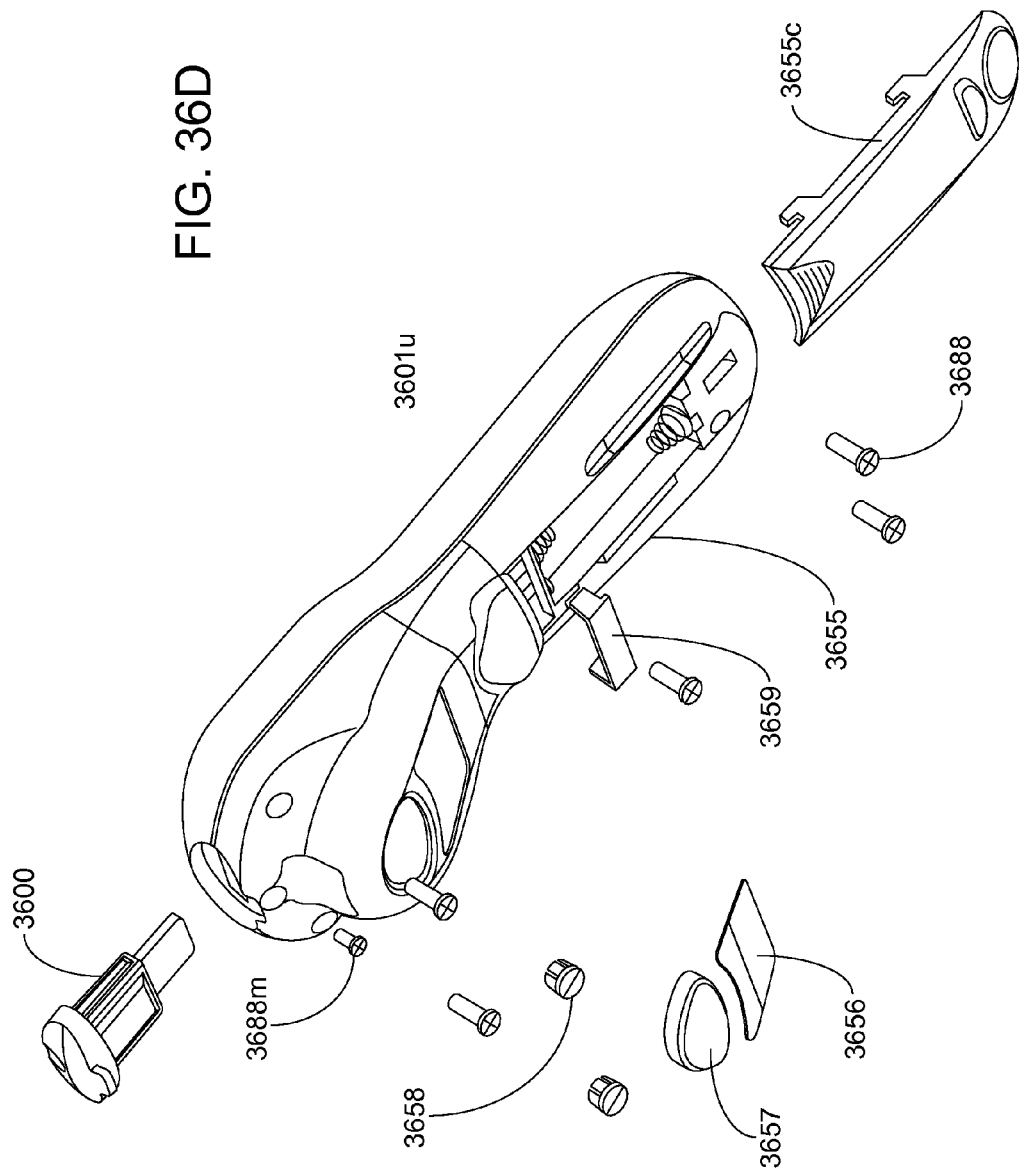

FIG. 36D illustrates the final assembly steps for the analyte measurement device. A replaceable strip port module 3600 is inserted within a receptacle formed by cut-outs in both the upper and bottom housing components 3601U, 3601B. A mounting screw 3688M is used to secure the module 3600 to the housing. Additional system components include an ergonomic pad 3657, a label 3656, plugs 3658, and cover 3659. Additionally, a battery compartment 3655 is provided with a battery contact 3692 and a battery cover 3655C.

The embodiments presented herein provide further advantages such as: the ability to upgrade strip port modules as new test strip technologies evolve; the ability to clean or sterilize a strip port module; and the ability to allow users to replace strip port modules without returning the entire measurement system to the manufacture.

Certain embodiments relate to in vivo (e.g., continuous monitoring) systems. A continuous monitoring system typically includes a sensor that is worn or placed below the skin, a transmitter that collects glucose information from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No. 6,175,752, which is hereby incorporated by reference in its entirety, discloses additional examples of a continuous monitoring system.

Embodiments of the present disclosure relate to components of a continuous monitoring system that may be replaceable. In one embodiment, the interface between the sensor and the transmitter may become contaminated. The transmitter or sensor control unit, for example, may have an interface with the sensor that has been molded to form a barrier between the transmitter's contacts and circuitry internal to the transmitter. This allows the transmitter's contacts to be washed without damaging the transmitter's circuitry. Alternatively, the contacts may be included in a replaceable port that can be replaced as needed. Similarly, the interface on the sensor may be molded to form a barrier to contamination or be replaceable.

In these examples, the strip connectors or ports can be used with continuous monitoring systems. As discussed herein, the sensor control unit or transmitter typically has a port to interface with the sensor. This port can be molded such that the contacts can be cleaned to prolong the MTBF. Alternatively, the port can be replaceable and/or washable. A replaceable port allows the continuous system to adapt to different sensor form factors.

Embodiments of the present disclosure further extend to kits. Examples of a kit include a measurement device with one or more strip connectors. In some kits, different strip connectors or ports for different types of strips may be included. This allows the measurement device to be used with different strip form factors. The kits may also include a plurality of test strips. In certain examples, the measurement device may be configured for use with disposable test strips as well as with test strips that are configured for continuous monitoring systems. Thus, the measurement device may include a receiver to receive information from a transmitter that collects glucose information from an inserted sensor. The measurement device may also include a strip connector, such as those disclosed herein, for use with single use test strips.

Barriers and Seals for Strip Ports and Analyte Measurement Devices

In some aspects of the present disclosure, a barrier device is provided that couples to a strip port of an analyte measurement device and serves to prevent liquids from traveling down the test strip and entering the strip port. In one embodiment, the barrier device removably couples to a strip port that is fixedly integrated within the analyte measurement device. In such case, the barrier device is shaped and sized to fit within the strip port and be maintained in the strip port until removed. The barrier device may include, for example, retention elements that cooperate with other retention elements on the strip port or measurement device to secure the barrier device in the strip port. Any variety of retention elements may be used, such as fasteners, latches, rivets, hoops, screws, tabs, etc., for example. The retention elements on the barrier device may also be configured to cooperate with existing elements in the strip port or on the analyte measurement device. For example, the barrier device may include retention elements that are shaped and sized to engage in an LED slot or other existing element in the strip port, or receptacle of the meter including the strip port.

In another embodiment, the barrier device may be integrated with a replaceable strip port module that removably couples to an analyte measurement device. The barrier device may be fixedly attached to the replaceable strip port module and remain as a single integrated and inseparable component of the strip port module. Alternatively the barrier device may be removably coupled to the replaceable strip port module such that it can be separated from the replaceable strip port module for cleaning or for replacement purposes, for example. An inserted test strip electrically couples the strip port module which is electrically coupled to the measurement device.

It should be appreciated that the barrier is not required to provide a completely liquid tight seal. In some instances, the barrier may serve to minimize any gap or opening so that surface tension would prevent additional penetration of liquid into the barrier and strip port.

In one embodiment, the barrier is reusable and sufficiently durable to be cleaned and disinfected or sterilized after each use for a multiple number of uses. In other embodiments, the barrier is for single use and disposable, and thus selecting an inexpensive material and components for the device may be desirable from a cost standpoint.

The barrier may be made from a variety of materials, for example, a polymeric material such as plastic, and/or an elastomeric material. A polymeric material may include a coating, such as an absorbent material and/or an elastomeric material. In some instances, the material should enable the barrier to be cleaned and disinfected with cleaning materials or solvents. In one embodiment, the barrier is made from an elastomeric material such as silicone, which is compatible with cleaning and disinfection for re-use. It should be appreciated that the barrier may vary in elasticity such as to provide varying degrees of rigidity while still remaining elastic.

In one embodiment, the barrier includes one or more protrusions, such as flaps, that are disposed near the strip port opening of the strip port connector. The flaps extend from the strip port and are configured to provide sufficient coverage of the strip port opening to protect the meter from contamination. For example, the strip port may include a front flange around the strip port opening of the strip port and have the one or more flaps extending from the front flange towards the strip port opening.

The flaps are configured to minimize test strips from getting "snagged" on the flaps when inserted into the strip port, which could bend or otherwise damage the contacts on the test strips upon insertion, for example. The flaps are also configured to not block the strip port opening. In some instances, the flaps are oriented to guide the test strip to the strip port opening of the strip port.

In one embodiment, the flaps are angled inward such that the end of the flaps near the strip port opening are further inside the strip port than the other end of the flaps connected to the front flange. In this way, the test strip may easily be inserted within the strip port opening while contacting the flaps without becoming obstructed by the flaps. It should be appreciated that in other embodiments, the flaps may be angled outward such that the end of the flaps connected to the front flange are further inside the strip port than the other end of the flaps near the strip port opening; or alternatively, not angled and extending straight down such that the end of the flaps connected to the front flange are approximately the same distance within the strip port than the other end of the flaps near the strip port opening.

In one embodiment, four flaps are included—a top flap, bottom flap, and two side flap, wherein the top flap, for example, coincides with the side of the test strip that receives the fluid sample. In another embodiment, two flaps are included—a top flap and a bottom flap, wherein the top flap, for example, coincides with the side of the test strip that receives the fluid sample. In yet another embodiment, a single flap provided, wherein the single flap coincides with the side of the test strip that receives the fluid sample. It should be appreciated that in other embodiments, other number of flaps may be included and oriented.

Figure 37A:
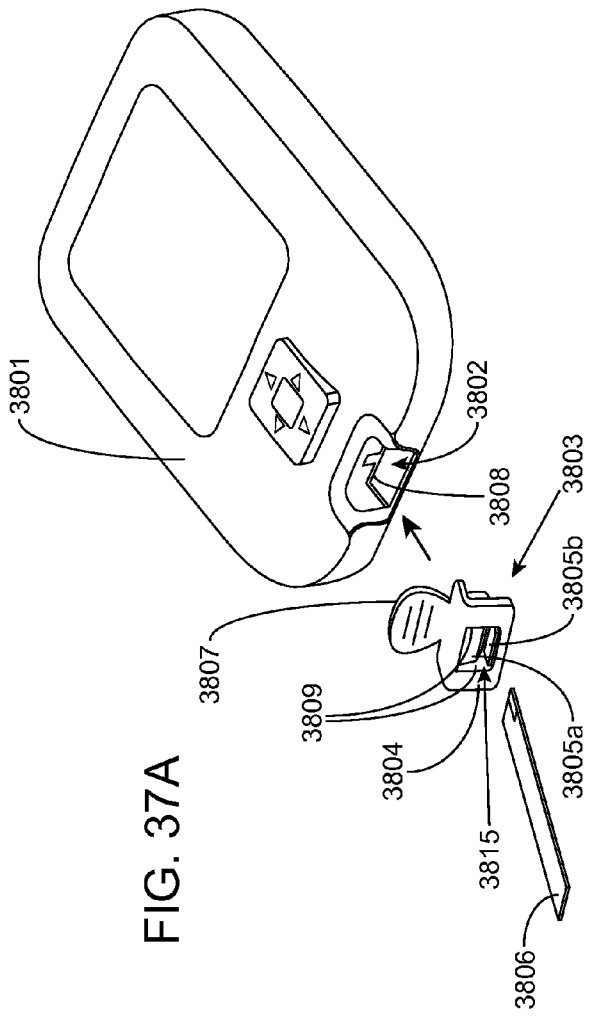
FIG. 37A illustrates a barrier, in accordance with an embodiment presented herein.

FIG. 37A illustrates a barrier, according to one embodiment. In the embodiment shown, a barrier device that is shaped and sized to removably and operably couple to a strip port of an analyte measurement device, such as a glucose meter for example. Meter 3801 includes a strip port 3802 that is configured to receive and operate with barrier device 3803. Barrier device 3803 includes a front flange 3804 around an aperture or slit 3815 that aligns with the strip port opening 3808 of the strip port 3802 when the barrier device 3803 is coupled to the strip port 3802. In this way, a test strip 3806 may be inserted within the aperture 3815 and through the strip port opening 3808 of the device 3801.

Barrier device 3803 is shown comprising sealing flaps 3805a,b extending from front flange 3804 inward toward the aperture 3815 (and strip port opening 3808 when coupled). The flaps 3805a,b are generally square or rectangular shaped, and may be trapezoidal shaped (e.g., with the shorter parallel side closest to the aperture 3815). It should be appreciated that in other embodiments, other varying shapes and sizes may be used.

Figure 37C:
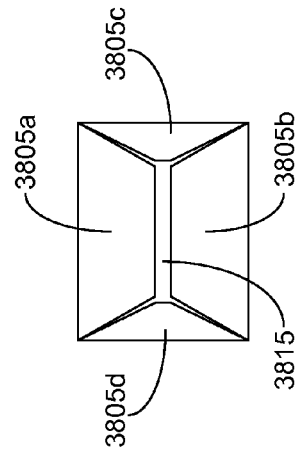
FIG. 37C, which illustrates a front view of a strip port having four barriers, according to one embodiment.
Figure 37B:
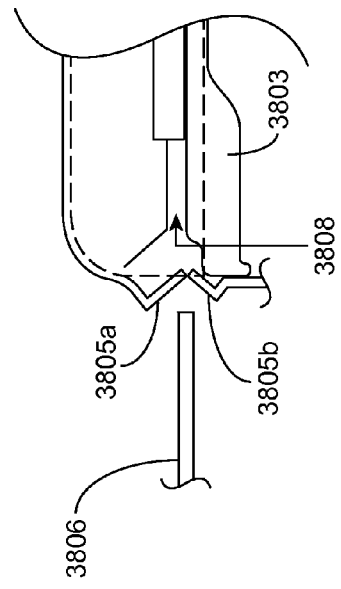
FIG. 37B illustrates a side view of the barrier device and strip port shown in FIG. 37A.

The inwardly extending flaps are shown in FIG. 37B, which illustrates a side view of the barrier device and strip port shown in FIG. 37A. The barrier device 3803 includes flaps 3805a,b which extend inwardly toward the aperture 3815 (and strip port opening 3808 when coupled). The flaps 3805a,b are oriented such that the center point between the ends is approximately aligned with the strip port opening 3808 when coupled.

The sealing flaps 3805a,b comprise a top flap 3805a and a bottom flap 3805b. The sealing flaps 3805a,b extend a sufficient distance to provide an approximate distance between the two flaps to receive a test strip 3806 and to slightly contact the test strip 3806. The distance may vary, and the more elastic the flaps 3805a,b are, the closer the two flaps may be to allow the test strip 3806 to push through the flaps 3805a,b. In one embodiment, the ends of flaps 3805a,b contact one another. In other embodiments, flaps 3805a,b do not necessarily contact the test strip 3806 but are sufficiently close to prevent contamination.

The flaps 3805a,b include a width that is approximately the width of the sidewalls 3809 of the strip port module 3803 to enable a barrier on the sides of the test strip. In other embodiments, the barrier may comprise side flaps, such as shown in FIG. 37C, which illustrates a front view of a strip port having four barriers, according to one embodiment. The side flaps 3805c,d are shown also angling inwardly towards the aperture 3815 (and strip port opening 3808 when coupled), and extending to the sides of the side flaps 3805a,b to prevent contamination from entering the strip port 3802 on the sides of the test strip 3806 when inserted within the strip port opening 3808.

The barrier may be disinfected or is disposable after use. For example, the barrier may be removed by a user and thereafter disinfected or thrown away. In some instances, the barrier may be disinfected or otherwise cleaned while still coupled to the measurement device. The barrier device includes a releasing element 3807 that enables the barrier device 3803 to be removed from the strip port 3802 of the device 3801. For example, the releasing element may be a finger tab that allows a user to grip with two fingers and pull, or otherwise disengage, the barrier device out of the strip port.

In some aspects of the present disclosure, a replaceable strip port module is provided. The replaceable strip port module may be internally sealed to contain fluid or other contaminants within the strip port module. For example, the strip port module may include a seal, gasket, or other seal-providing element around the strip port opening, for instance, to provide a seal with an inserted test strip. In one embodiment, the replaceable strip port module may be removed and cleaned and/or soaked in cleaning solution, and re-used thereafter.

Figure 38:
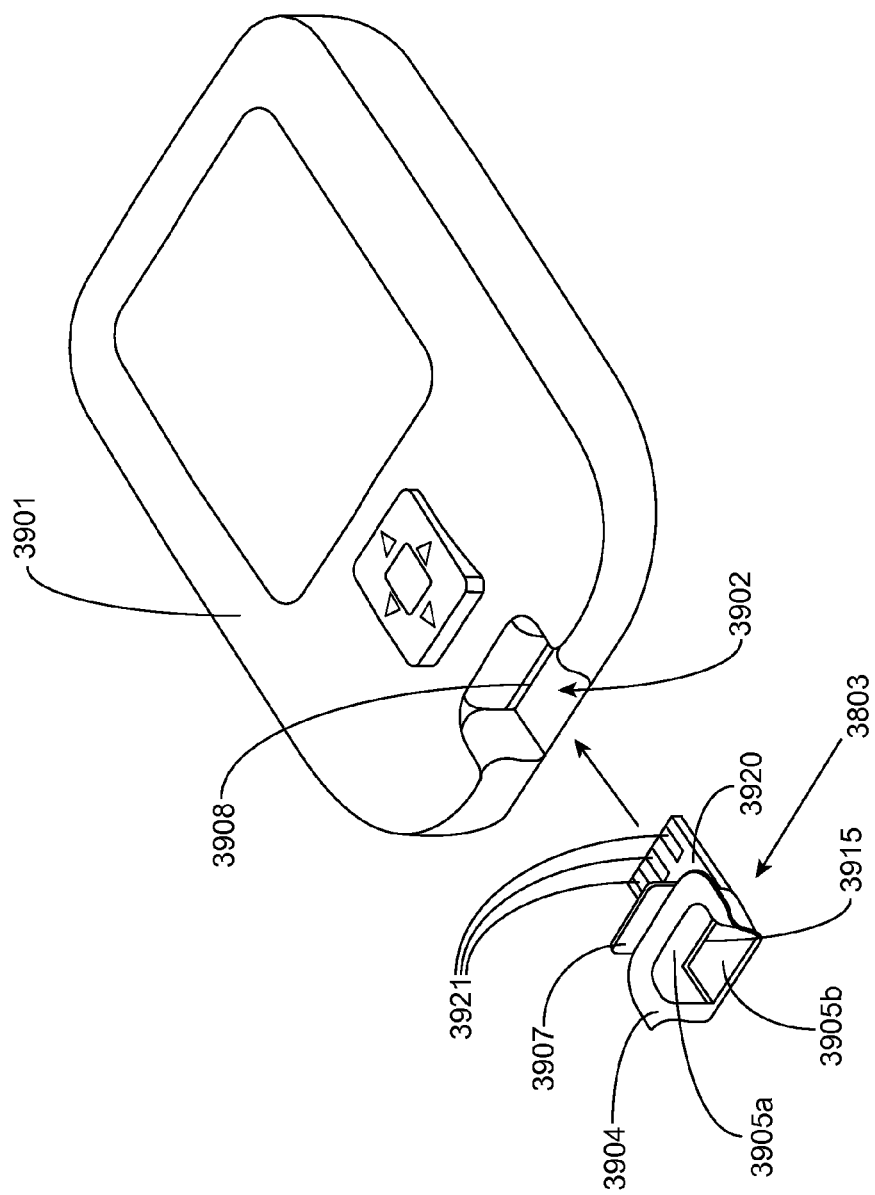
FIG. 38 illustrates a replaceable strip port module, in accordance with an embodiment presented herein.

FIG. 38 illustrates a replaceable strip port module, according to one embodiment. Replaceable strip port module 3903 removably and electrically couples to the strip port receptacle 3902 of analyte measurement device 3901. As shown, the opening 3908 of the strip port receptacle 3902 is not sealed and may enable fluid or other contaminants from entering the strip port when the replaceable strip port module 3903 is not coupled.

The strip port module 3903 may snap in the device 3901, or otherwise securely engage the strip port receptacle 3902. For example, the replaceable strip port module 3903 of the embodiment shown also includes connector 3920 that mates with the opening or socket 3908 of the strip port receptacle 3902 of analyte measurement device 3901. Additional retention elements, such as described above, may also be used to further secure the replaceable strip port module 3903 within the strip port receptacle 3902. The module 3903 may "snap" into the device 3900 and make electrical connection.

The contacts 3920 may take the form of conductive pads, which are contacted by contact fingers disposed on the measurement device 3900 to "wipe" the contacts 3920 as the connector 3920 is passed by the fingers into the receptacle 3902.

As the strip port module 3903 is sealed internally, any fluid within the strip port module cannot travel to the strip port receptacle 3902 and contaminate the meter electronics. Furthermore, when coupled, the replaceable strip port module 3903 serves as a barrier that sufficiently seals the strip port receptacle 3902 from fluid or other contaminants. In the embodiment shown, the strip port connector 3920 includes a substrate with contacts 3921 that enable electrical coupling with the strip port 3902 of the device 3901 to provide for an electrical connection between the strip port 3902 and the test strip.

As stated above, the interior of the strip port module 3903 is sealed to contain liquids within the module 3903. Furthermore, the strip port module 3903 shown includes flanges that provide additional surface area around the opening for the test strip to keep the strip port module and meter free from contamination.

In the embodiment shown, the replaceable strip port module 3903 includes a front flange 3904 having surfaces 3905a,b which surround an aperture or strip port opening 3915 for a test strip to be inserted through. In another embodiment, the surfaces 3905a,b are flaps, such as those described in FIGS. 37A-C.

Furthermore, replaceable strip port module 3903 may be removed by a user and thereafter disinfected or thrown away. For example, the replaceable strip port module 3903 may be soaked in a cleaning solution or disinfectant solution and then dried thereafter before being recoupled to the measurement device for re-use. Any plastic, metal contacts, and electrical connection pad materials may be selected to be compatible with cleaning and disinfecting solutions. In some instances, the replaceable strip port module 3903 may be disinfected or otherwise cleaned while still coupled to the measurement device. The external surfaces of the strip port and measurement device may be wiped down to keep the remainder of the analyte measurement device clean.

The replaceable strip port module 3903 is shown including a releasing element 3907 that enables the replaceable strip port module 3903 to be removed from the strip port receptacle 3902 of the device 3901. For example, the releasing element may be a finger tab that allows a user to grip with two fingers and pull, or otherwise disengage, the replaceable strip port module 3903 device out of the strip port receptacle 3902.

It should be appreciated that the replaceable strip port module may be replaced with another replaceable strip port module after multiple uses, or after the replaceable strip port module is too contaminated for cleaning, or to be used while the strip port module is being cleaned or disinfected.

In multi-patient use, the replaceable strip port module may be cycled so that the disinfected strip ports are used once per patient and then removed for cleaning and disinfection again, for example. To control the number of use/cleaning cycles, complete batches of replaceable strip port modules may be replaced at selected intervals (e.g., 3 months, 6 months, or 12 months, depending on the frequency of re-use) for example. This may also apply to single patient use, allowing the user to clean and disinfect the replaceable strip port module when desired and then re-install the strip port module in the meter.

In some aspects of the present disclosure, an analyte measurement device includes a strip port that is internally sealed and also sealed with respect to the meter, such as with a gasket between the strip port and housing. In this way, a sufficiently liquid tight seal is provided that permits the strip port to be soaked or flushed in place on the measurement device, even though other parts of the measurement device may not be sealed. It should be appreciated that while the rest of the meter is not required to be sealed, in embodiments providing as much sealing and protection as possible in the measuring device minimizes the chance of accidentally damaging the meter while cleaning.

For example, the strip port can be soaked with a cleaning or disinfecting solution (e.g., from an eyedropper or other application device) and left to soak for some time to thoroughly clean the strip port before being shaken and/or poured out and let dry. As the strip port is internally sealed, the strip port electronics are protected from contamination. The measurement device may then be wiped to eliminate any stray fluid. In some instances, maintaining the measuring device at a certain position or angle may minimize the risk of liquid intrusion into the meter. Instructions advising the user of such position or angle may be provided to the user, for example. In one embodiment, the strip port is angled within the housing of the measuring device in a position to facilitate drainage of cleaning solution.

Figure 39:
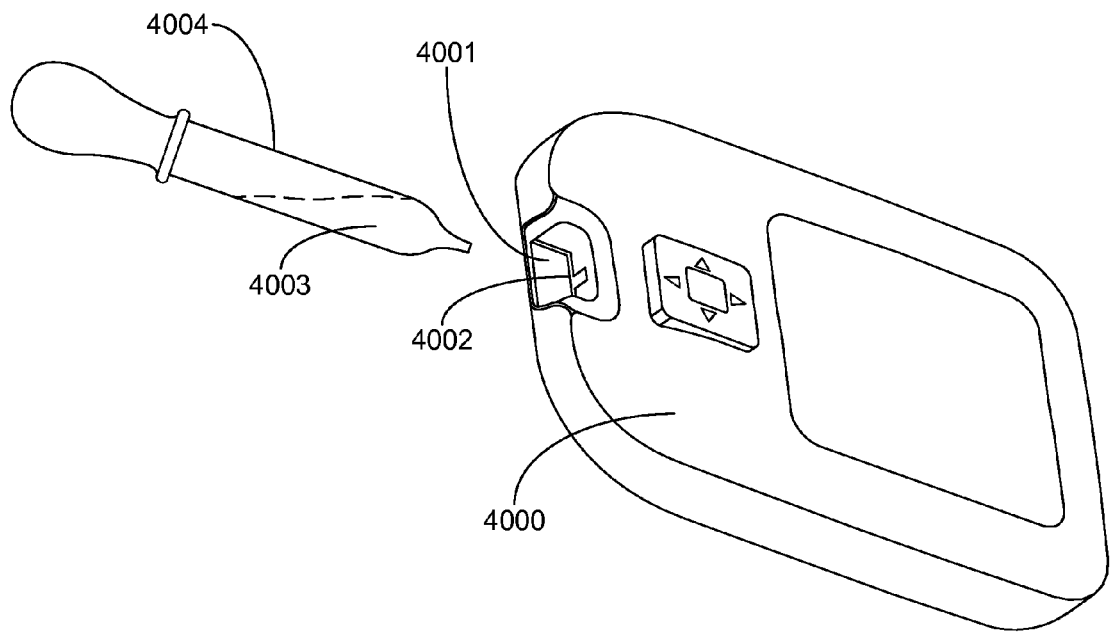
FIG. 39 illustrates a meter including a strip port that includes a seal and gasket, in accordance with an embodiment presented herein.

FIG. 39 illustrates an analyte measurement device 4000 including a strip port 4001 that is internally sealed and sealed with respect to the rest of the device, according to one embodiment. Because strip port 4001 is internally sealed, liquid entering the strip port 4001 is prevented from entering further into the device 4000 via the strip port 4001. Eye dropper 4004 includes disinfecting solution 4003 and is used to apply disinfecting solution 4003 within the strip port 4001 of device 4000 to clean the strip port 4000 of contaminants. The strip port 4001 may then be soaked, for example, and later drained. Since the strip port 4001 is sealed with respect to the housing of the device 4000, fluid cannot enter device around the strip port 4001 and contaminate the meter electronics.

Figure 40:
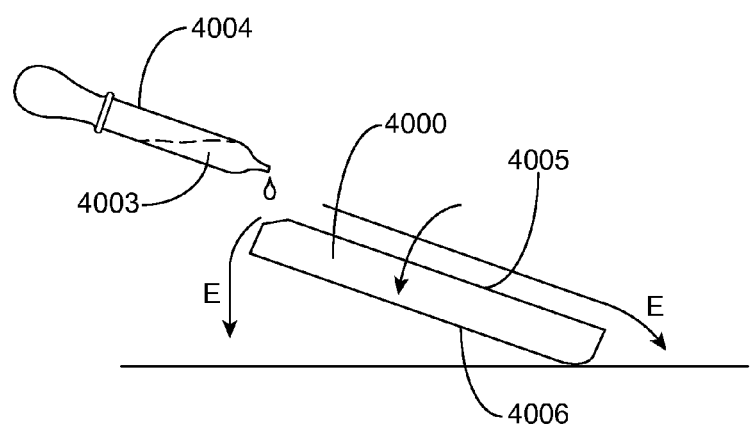
FIG. 40 illustrates fluid flowing off an analyte measurement device, according to one embodiment.

It should be appreciated that in such case the remainder of the measurement device should be carefully designed to prevent liquid from entering unsealed portions of the meter, such as control buttons or battery compartment for example. FIG. 40 illustrates fluid flowing off an analyte measurement device, according to one embodiment. Meter 4001 includes one side 4005 that does not contain any unsealed areas of the device (e.g., the bottom of the device that includes only the housing of the device), and another side 4006 that includes one or more unsealed portions of the device, such as buttons, connection ports, etc. To avoid intrusion of the disinfecting solution into the unsealed portions, the device 400 is oriented with the side 4005 facing up to allow any excess disinfecting solution that does not enter the strip port 4001 to roll off sealed portions of the device 4000, such as side 4005, as shown by directional arrows E.

In some aspects of the present disclosure, a sealed strip port is provided that enables liquid cleaning or disinfecting solution to "flow through" the strip port. In one embodiment, the port is sealed to prevent intrusion into the housing, but allows solution to be flow or flush through the port and drain out an outlet of the measurement device. In this way, the strip port may be flushed out to provide a more thorough cleaning.

Figure 41A:
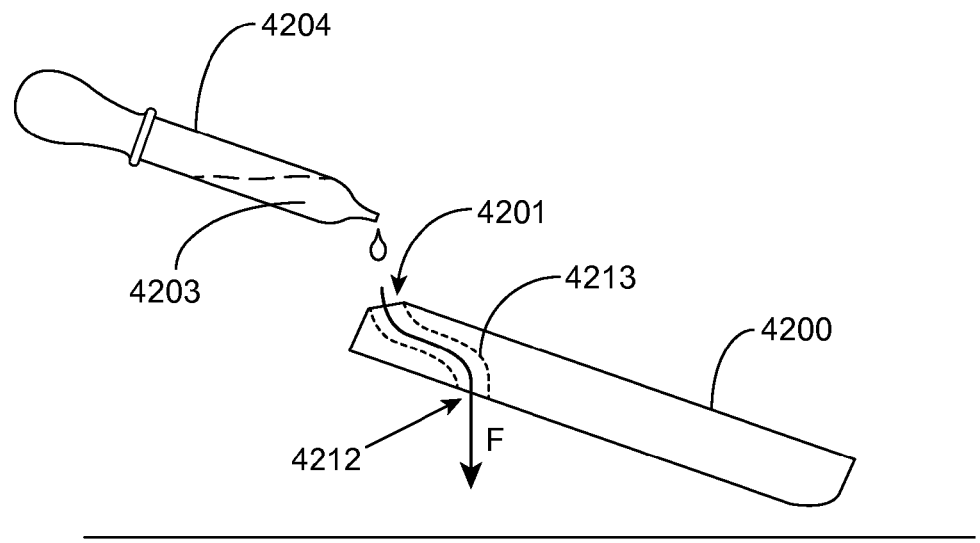
FIGS. 41A-B illustrate a sealed port that permits solution to flow through the strip port, according to two different embodiments.
Figure 41B:
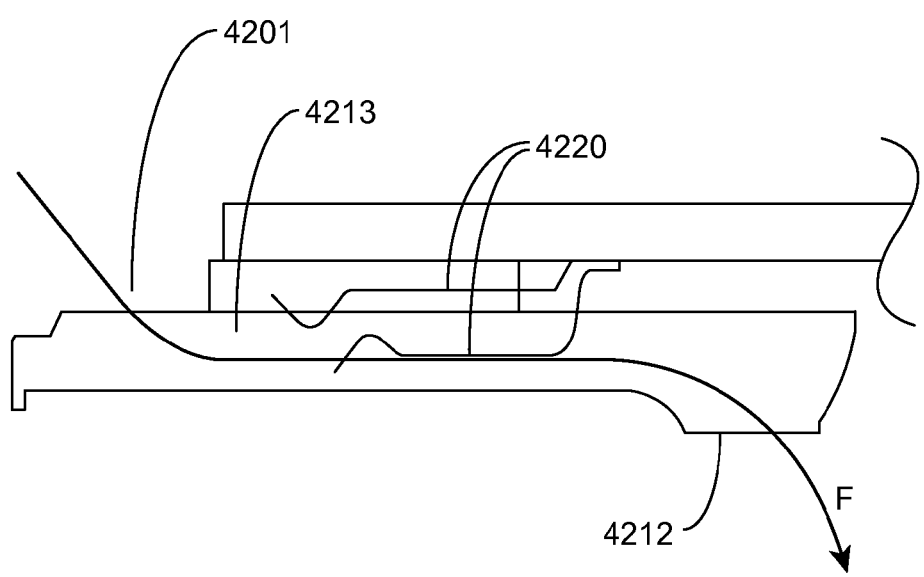

For example, FIGS. 41A-B illustrate a strip port that permits solution to flow through the strip port, according to two embodiments. Analyte measurement device 4200 includes a strip port 4201 that provides a sealed path 4213 within and through the device 4200 to an outlet 4212 disposed in the housing. In this way, solution 4203 from eye dropper 4204 is applied within strip port 4201 and allowed to flow through the sealed path 4213 and out the outlet 4212 in the housing to avoid possible external exposure of the contacts (mechanical, ESD, etc.), as represented by directional arrow F.

The remainder of the device 4200 remains sealed from the strip port and sealed path, to prevent intrusion of the solution into the rest of the device 4200. In FIG. 41A, the sealed path 4213 is generally straight through one end of the device to allow the fluid to flow through the device 4200 to the outlet 4212. In FIG. 41B, the sealed path 4213 extends sideways for a more significant distance within the device—e.g., along the longitudinal axis of the device 4200 and parallel to printed circuit boards within the device 4200. In one embodiment, certain contacts 4220 are exposed to the cleaning solution to clean the contacts. It should be appreciated that the sealed path may be directed in one or more directions to provide the most advantageous path for a minimum chance of intrusion or otherwise improper contact with unprotected portions of the device.

In some instances, a stand or other fixture may be used to keep the measurement device in the correct position or angle to minimize the risk of intrusion into a non-sealed portion of the measurement device.

In some aspects of the present disclosure, an analyte measurement device is provided that is entirely and sufficiently liquid tight sealed to permit the device to be fully or significantly submerged into a liquid, such as a cleaning or disinfecting solution. The measurement device would thus be disinfected by soaking, and the meter must be sufficiently liquid tight sealed to prevent intrusion of liquid within inappropriate parts of the device when submerged in shallow solutions. It should be appreciated that the interfaces of the measuring device may be selected or modified accordingly to provide such a liquid tight seal. For example, some interfaces, such as jog wheels or connector openings may be limited to reduce the number of seals. For example, wireless connections may be used in place of wired connections to eliminate connection ports. In some instances, connector opening may include a sealing cover—e.g., a rubber cover that fits within the connector opening to block the connector opening from fluid. Battery compartments covers may be sealed to prevent fluid from entering the battery compartment. In some instances, rechargeable batteries may be used to eliminate having sealed battery compartment covers.

Figure 42:
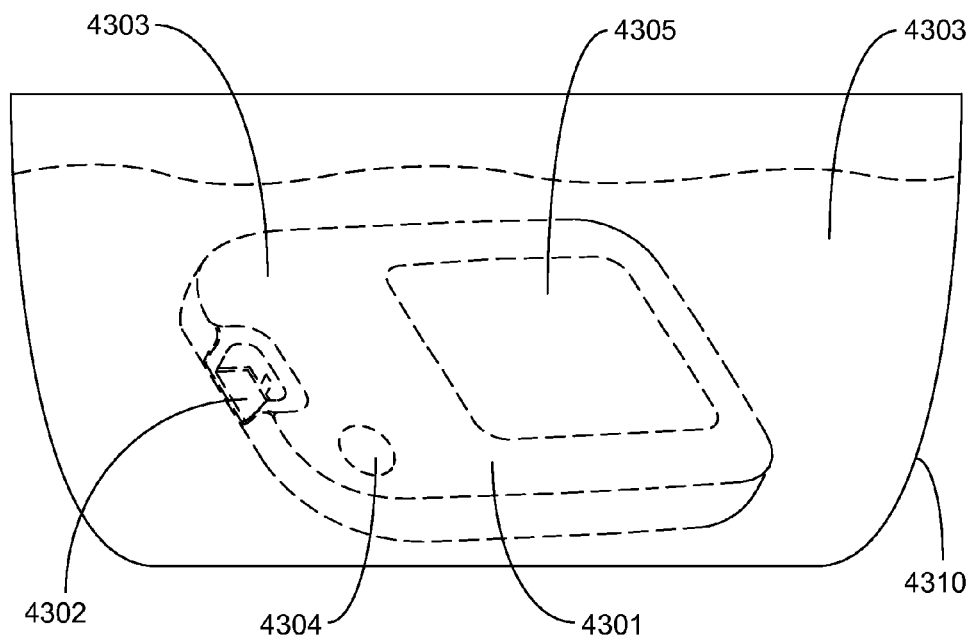
FIG. 42 illustrates a sealed analyte measurement device submerged in fluid, in accordance with an embodiment presented herein.

FIG. 42 illustrates a sealed analyte measurement device submerged in fluid (e.g., cleaning or disinfecting solution), according to one embodiment. As shown, measurement device 4300 is fully submerged into a shallow volume of disinfecting solution 4303 contained in a container 4310. Device 4300 includes strip port 4302, buttons 4304, display 4305, which are all disposed within housing 4303. Each of the components are sealed with respect to itself as well as with respect to the housing to prevent intrusion of fluid within the device 4300. Other components not shown may also be sealed if present, such as battery compartment cover, communication ports (e.g., USB or Bluetooth ports). Any sealing material or elements may be used, such as elastomeric materials, rubber seals, gaskets, and/or sealing films and coatings, etc.

Analyte measurement devices may be used in hospitals or other health care facilities, and furthermore, used with multiple users and/or across multiple departments in the facility. In some aspects of the present disclosure, a covered analyte measurement device is provided that includes a cover material or layer that seals or otherwise protects the analyte measurement device from microbes or other contaminants. The covered analyte measurement device is thus microbially resistant in the sense that the cover material facilitates cleaning of the device to reduce cross contamination—e.g., from use with multiple users—from a variety of potentially dangerous bacteria such as Methicillin-Resistant Staphylococcus Aureus (MRSA).

In one embodiment, the cover material is one contiguous see through skin which covers the analyte measurement device and its susceptible components of the analyte measurement device—e.g., any buttons, battery cover, screen, case joints, etc. In another embodiment, the cover material does not cover the entire device, but only the susceptible components of the device.

The cover material provides an opening for the strip port to enable a test strip to be inserted into the strip port. The opening may be, for example, a sleeve that minimizes access to only when a test strip is inserted. The cover material may be made from any variety of materials that enable the cover to be cleaned and that are semi-transparent or fully-transparent. For example, in one embodiment the cover material is silicone.

In one embodiment, the cover is made from a material, or includes a coating, that changes color when wet with alcohol, such as from an alcohol swab or pad that is used to clean the cover material. In another embodiment, the cover is made from a material that becomes clear (e.g., from semi-opaque or fully opaque for example) when wet through a cleaning protocol (e.g., from a cleaning or disinfectant solution), and thus allowing or facilitating use. In yet another embodiment, a message or icon indicating instructions to clean the device is provided or displayed—e.g., a "clean me" message displayed on the display of the measurement device. The device may be programmed not to work, for example, to require acknowledgement in such case, and further, may not permit the device from being used without acknowledgement (e.g., that the device is cleaned).

Cleaning Tool

In some aspects of the present disclosure, a strip port cleaning tool is also provided. The cleaning tool enables a user to gently rub the contact surfaces of the strip port contacts and remove any solids that may have dried onto the contacts, for example. The strip port cleaning tool is shaped and sized to facilitate cleaning of the strip port (e.g., replaceable strip port module or fixedly attached strip port) of an analyte measurement device. For example, in one embodiment, the cleaning tool includes a handle and an end shaped like a test strip to insert into the strip port. The material of the tool may vary, but should provide a mild abrasive so that contact surfaces are cleaned but not damaged. The thickness is important to ensure the strip port contacts are not damaged during use of the tool. Using the tool after soaking the strip port to first soften any dried material may assist with the cleaning process. The strip shaped end of the tool may, in some instances, be dipped in a solution prior to inserting into an internally sealed strip port. The solution may clean the tool and/or provide the tool with solution for cleaning the strip port. The tool may be die-cut, for example, from materials (e.g., paper, plastic, etc.) laminated too provide the appropriate cleaning, absorbent, abrasive surface and mechanical rigidity. In one embodiment, the tool may include two ends, on for wet cleaning and one for dry rubbing afterwards. The wet cleaning end may be semi-absorbent and semi-abrasive for example to retain some cleaning solution for application to the strip port. The dry cleaning end may be absorbent and less abrasive for example to facilitate dry rubbing.

Figure 43:
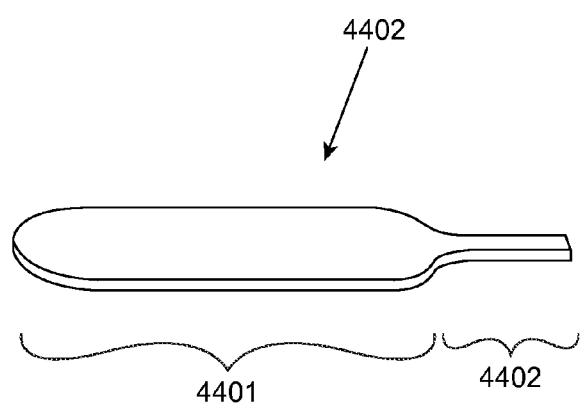
FIG. 43 illustrates a cleaning tool for a strip port of analyte measurement device, in accordance with an embodiment presented herein.

FIG. 43 illustrates a cleaning tool for a strip port of analyte measurement device, according to one embodiment. As shown, cleaning tool 440 includes a handle 4401 that is shaped and sized to be held by a user. The shape may vary but should be conducive to being comfortably gripped by the user for manipulation and use of the tool. The tool 4400 also includes a cleaning portion 4402 that extends from the handle and is shaped and sized similar to a test strip and such that it may fit within the strip port opening of the strip port. The cleaning portion 4402 may thus be inserted into the strip port opening to clean the contacts. In one embodiment, the width and thickness of the cleaning portion closely approximates the width and thickness of the test strip to facilitate cleaning of the contacts without damaging the strip port. The width and thickness may be slightly smaller than that of the test strip to enable the cleaning portion to enable some movement for rubbing or cleaning.

Strip Port Interface

In some aspects of the present disclosure, a strip port interface is provided that protects an analyte measurement device from fluid ingress into the device. Fluid ingress is a function of both of the potential energy needed to enter the meter, as well as the potential energy of taking alternative routes. By providing alternative paths, for example, fluid ingress can be minimized without being constrained to making the strip and strip port opening as tight a fit as possible, which may lead to difficulty in inserting the test strip.

The strip port interface is configured to couple to the strip port of an analyte measurement device. In one embodiment, the strip port interface is fixedly attached to the measurement device and integral to the strip port. In another embodiment, the strip port interface is removably coupleable to the device.

A test strip is inserted through the strip port interface and then through the strip port opening to electrically contact the strip port electronics. The strip port interface wicks any fluid (e.g., traveling along the test strip and toward the strip port opening) away from the strip port opening of the strip port of the measurement device to prevent fluid from entering the strip port and contaminating strip port electronics. The interface provides alternative paths and may additionally utilize capillary action to draw fluid away from the strip port opening along the alternative paths. In one embodiment, paths are provided for displacing air to escape as fluid enters the strip port interface. This reduces the pressure potential, for example, to assist with guiding the fluid away from the strip port.

Figure 44C:
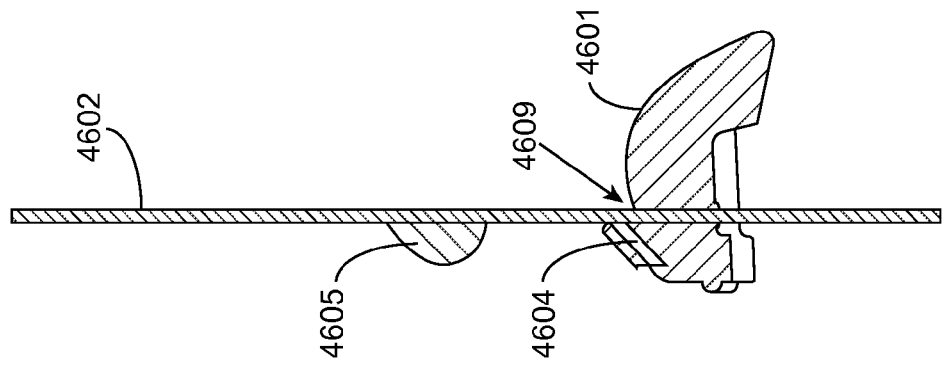
FIGS. 44A-C illustrate a fluid wicking interface, in accordance with an embodiment presented herein.
Figure 44B:
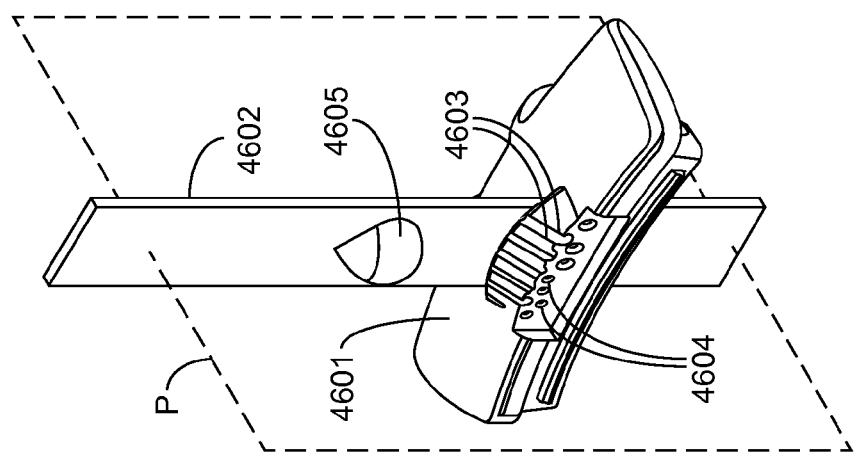
Figure 44A:
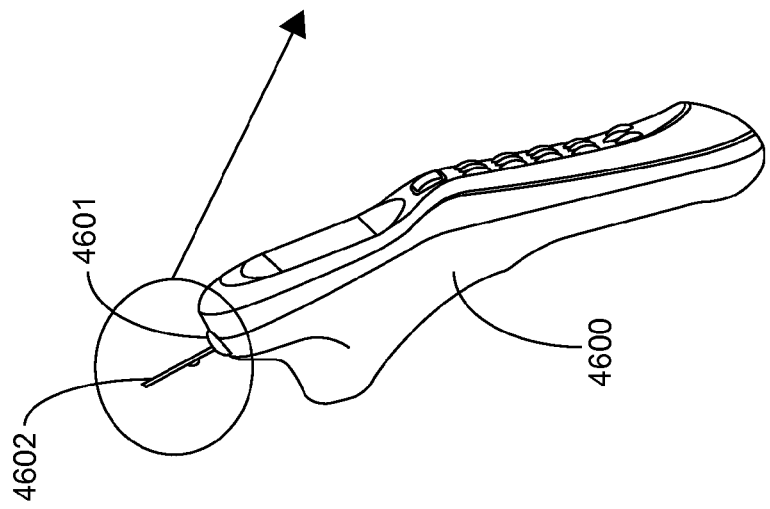

FIGS. 44A-C illustrate a strip port interface, according to one embodiment. FIG. 44A illustrates a strip port interface coupled to an analyte measurement device. FIG. 44B illustrates a perspective view of the strip port interface with a test strip inserted therein (shown without the analyte measurement device). FIG. 44C illustrates a cross sectional side view of the strip port interface and test strip shown in FIG. 44B, along plane P.

The strip port interface 4601 is fixedly attached to analyte measurement device 4600 and receives a test strip 4602. Strip port interface 4601 includes paths 4603 and 4604 formed within the interface around the aperture 4609 of the interface in which the test strip is inserted. The paths 4603 are formed on the exterior surface of the strip port interface 4601 near the aperture, and the paths 4604 are formed below the exterior surface of the fluid wicking interface 4601 near the aperture. The paths are aligned generally along the direction of gravity. The paths may be formed as narrow paths sized for capillary action to wick away fluid from the strip port opening. For example, fluid 4605 traveling along the test strip 4602 towards the aperture 4609 contacts paths 4603 and is wicked via capillary action along paths 4603 away from the strip port opening of the device. Any fluid 4605 that is not guided along path 4603 then encounters paths 4604 and is wicked via capillary action, or otherwise guided along path 4604. The fluid may be guided, for example, external to the device (e.g., off to the side of the device), etc.

In one embodiment, some or all of the paths 4604 serve to displace air to escape as fluid enters the strip port interface. In this way, the pressure potential is reduced, for example, to assist with guiding the fluid away from the strip port. It should be appreciated that in some embodiments, the paths may serve both purposes of guiding fluid away, as well as displacing air.

Figure 45C:
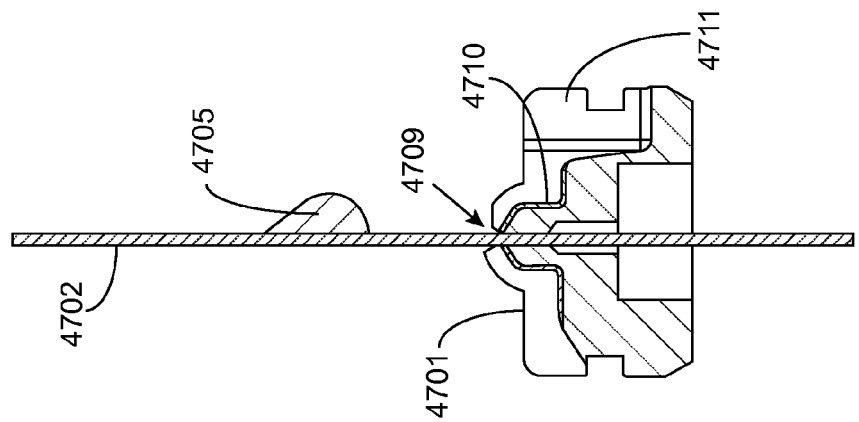
FIGS. 45A-C illustrate a fluid wicking interface, in accordance with an embodiment presented herein.
Figure 45B:
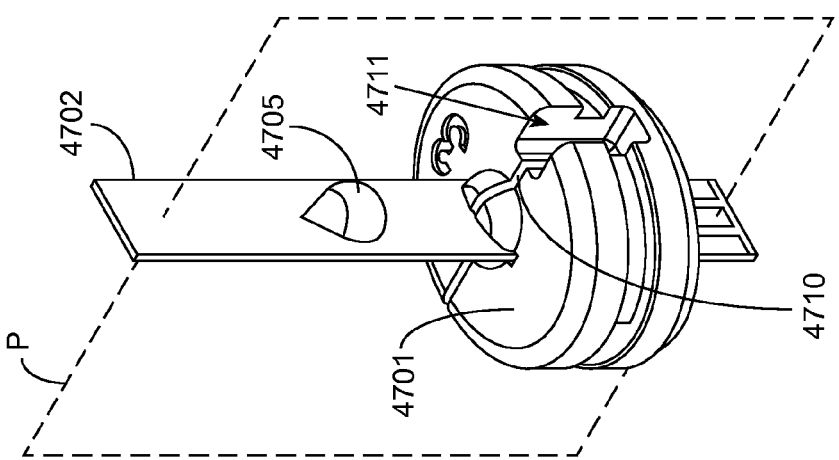
Figure 45A:
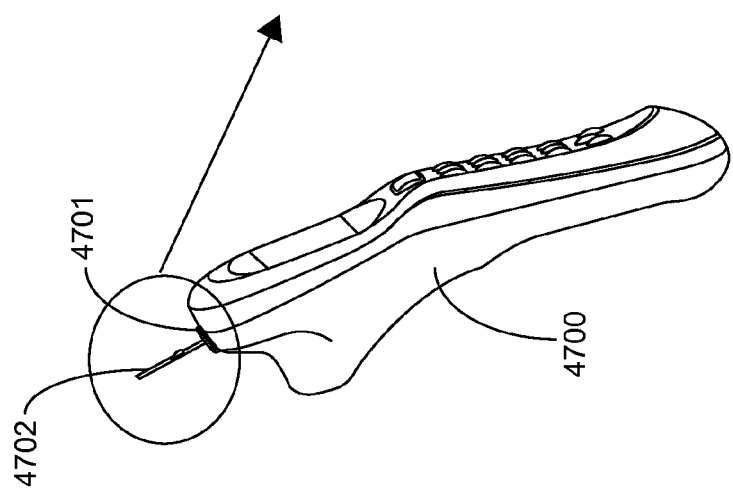

FIGS. 45A-C illustrate a strip port interface, according to one embodiment. FIG. 45A illustrates a strip port interface coupled to an analyte measurement device. FIG. 45B illustrates a perspective view of the strip port interface with a test strip inserted therein (shown without the analyte measurement device). FIG. 45C illustrates a cross sectional side view of the strip port interface and test strip shown in FIG. 45B, along plane P.

The strip port interface 4701 is fixedly attached to analyte measurement device 4700 and receives a test strip 4702. Strip port interface 4701 includes path 4710 (e.g., narrow groove) formed within the interface around the aperture 4709 of the interface in which the test strip is inserted. The path 4710 extends along plane P from the aperture 4709 outward to a reservoir 4711. Fluid 4705 traveling along the test strip 4702 towards the aperture 4709 contacts the path 4710 and is guided along path 4710 into reservoir 4711. The fluid may accumulate with reservoir 4711 or be guided away from the strip port opening of the device. In some instances, the path or narrow groove is sized for capillary action to wick the fluid away from the strip port opening.

Figure 46C:
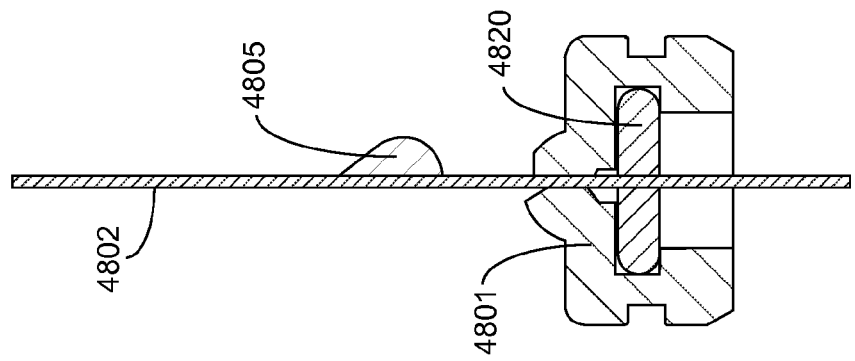
FIGS. 46A-C illustrate a fluid wicking interface, in accordance with an embodiment presented herein.
Figure 46B:
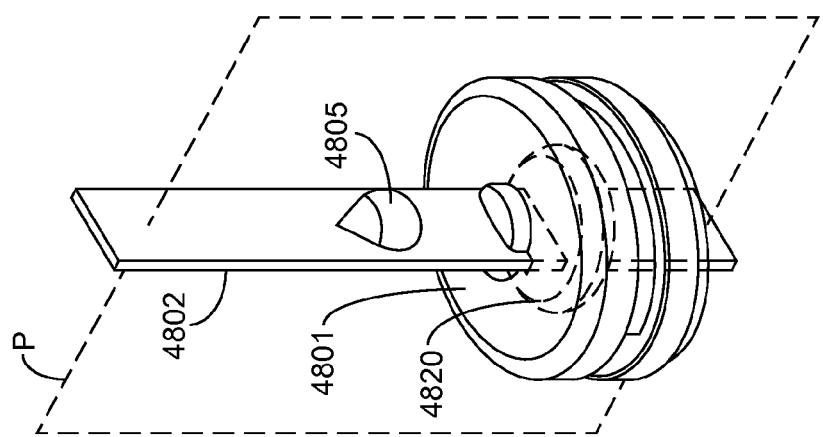
Figure 46A:
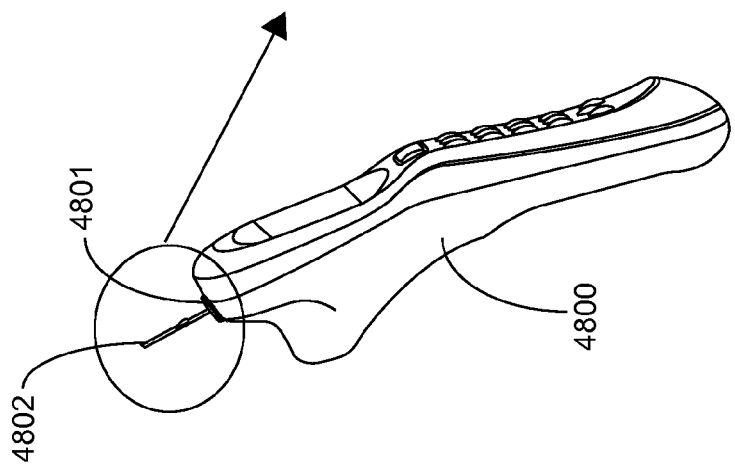

FIGS. 46A-C illustrate a strip port interface, according to another embodiment. FIG. 46A illustrates a strip port interface coupled to an analyte measurement device. FIG. 46B illustrates a perspective view of the strip port interface with a test strip inserted therein (shown without the analyte measurement device). FIG. 46C illustrates a cross sectional side view of the strip port interface and test strip shown in FIG. 46B, along plane P.

The strip port interface 4801 is fixedly attached to analyte measurement device 4800 and receives a test strip 4802. Strip port interface 4801 includes an absorbent insert 4820 that is disposed within the interface at or near the aperture of the interface in which the test strip is inserted. The absorbent insert 4820 is positioned to come in contact with, or be very close to, the test strip 4802 such that any fluid 4805 traveling along the test strip contacts the insert 4820 and is absorbed and prevented from continuing within the strip port. The absorbent insert 4820 may include a hole or slit within the insert 4820 that forms an aperture for the test strip 4805 to pass through. The absorbent insert 4820 may be made from any variety of absorbent materials. The amount of absorbent material may vary but should sufficient enough to absorb at least an approximate sample amount. While the absorbent material is circular in the embodiment shown, it should be appreciated that other shapes and sizes may be implemented in other embodiments.

In one embodiment the interface is integrated within the strip port and non-removable. The strip port may be integrated within the analyte measurement device or be a replaceable strip port module that may be removably coupled to the measurement device. For example, in one embodiment the strip port interface is integrated within a cap of a replaceable strip port module, such as one described in previous sections.

The strip port interface may be made from any variety of materials. In one embodiment, the interface is a wipeable material such as a polymeric material (e.g., plastic), one or more metals or metal-alloys, glass, etc. In another embodiment, the interface may be made from an absorbent material, which may be disposed of after use, for example. The strip port interface may be made from materials that are hydrophilic or that include a hydrophilic coating. In one embodiment, the strip port interface is made from a material that changes color when wet to indicate that device is contaminated.

Absorptive Elements

While fluid samples, such as blood, is needed to interact with the chemistry of a test strip, excess fluid should not enter the measurement device and contaminate the device. In some aspects of the present disclosure, one or more absorptive elements are provided that are configured to couple to the entrance of a strip port in order to prevent liquids or other contaminants from entering the strip port and damaging electronics therein.

In some instances, the one or more absorptive elements are included on an absorptive guard coupled to the strip port such that the absorptive elements are positioned to contact the test strip to absorb any excess fluid approaching the strip port opening. The absorptive element may be made of any material that absorbs fluid. When one absorptive element is used, the absorptive element is positioned to coincide with the side of the test strip that the fluid sample is applied. In one embodiment, absorptive guard comprises two absorptive elements that are positioned such that the test strip enters between the two absorptive elements in order to enter the strip port opening. In this way, the two absorptive elements are disposed on opposite sides of the major surfaces of the test strip to ensure that any fluid flowing down the body of the test strip is absorbed by an absorptive element. Having absorptive elements on both of the major surface sides of the test strip ensures that an absorptive element is positioned on the fluid receiving side of the test strip, regardless of which way the test strip is inserted into the strip port. Furthermore, if any excess fluid is accidently applied to the opposite side than the fluid receiving side and then flows down the test strip, the other absorptive element will absorb the fluid and prevent the strip port electronics from being contaminated.

In one embodiment, the absorptive elements may be removable from the absorptive guard to enable the absorptive elements to be cleaned and/or replaced with new absorptive elements. In such case, the absorptive guard includes a frame and securing element that secures the absorptive element to the frame when coupled. The absorptive guard includes retaining elements that are used to couple and maintain the absorptive guard to the strip port. The strip port may be integrally formed within an analyte monitoring device or may be a replaceable strip port module that removably couples to the device.

In another embodiment, the absorptive elements are fixedly attached to the absorptive guard and the absorptive guard is removably coupled to the strip port when the absorptive guard is cleaned and/or replaced with a new absorptive guard.

Figure 47A:
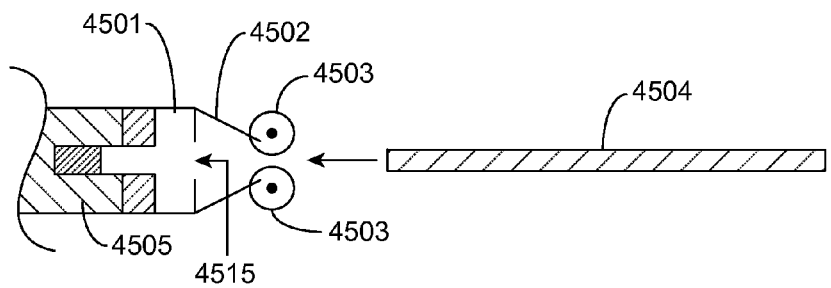
FIGS. 47A-D illustrates a test strip at various points when being inserted into a strip port having an absorptive guard coupled thereto, in accordance with an embodiment presented herein.
Figure 47B:
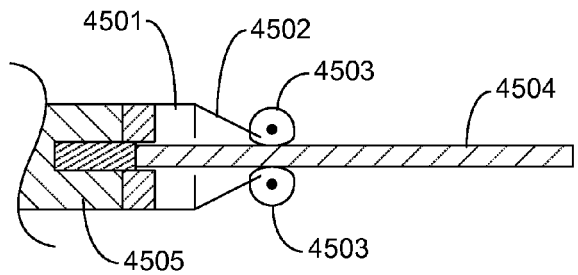
Figure 47C:
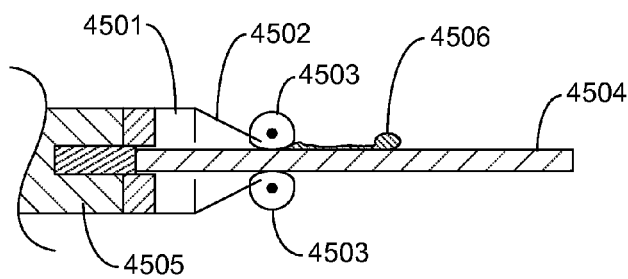
Figure 47D:
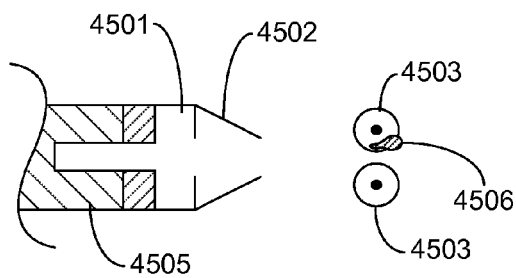

FIGS. 47A-D illustrates a test strip at various points when being inserted into a strip port having an absorptive guard coupled thereto, according to one embodiment. Strip port 4501 includes strip port electronics 4505 disposed inside, and an absorptive guard coupled to the entry of the strip port 4501. In the embodiment shown, the absorptive guard is fixedly attached to the strip port, but may be removably coupled to the strip port in other embodiments. Absorptive elements 4503 are removably coupled to the absorptive guard 4502—e.g., via securing elements (not shown) such as fasteners, latches, rivets, hoops, screws, tabs, etc. The absorptive elements 4503 are positioned on the absorptive guard 4502 and aligned with the strip port opening 4515 such that a test strip 4505 must be inserted between the absorptive elements 4503 to enter the strip port 4501. As shown in FIG. 47A, the absorptive elements 4503 are positioned to receive the test strip 4504. The test strip is inserted in between the absorptive elements 4503 and through the strip port opening 4515 of the strip port 4501 to electrically couple to the strip port electronics 4505, as shown in FIG. 47B. If fluid 4506, such as excess sample fluid, flows along the test strip 4504 towards the strip port 4501, the fluid 4506 contacts the absorptive elements 4503 and prevented from entering the strip port and contaminating the strip port electronics, as shown in FIG. 47C. The test strip 4504 may then be removed after the measurement is performed by the analyte measurement device. The absorptive elements 4503 may then be removed from the absorptive guard, as shown in FIG. 47D, to be cleaned and/or disposed of such that new absorptive elements may be coupled for use.

It should be appreciated that the entire absorptive guard may be replaced in other embodiments, such that the entire absorptive guard may be cleaned or disposed of. It should also be appreciated that in other embodiments, the absorptive elements may be coupled directly to the strip port, without an absorptive guard including a frame in which the absorptive elements couple.

Orientation Detection

A common failure for some analyte measurement devices is the application of control solution such that the solution is gravity fed into the strip port connector. Such intrusion into the strip port may make the device inoperable or otherwise damage the device. In some aspects of the present disclosure, an analyte measurement device is provided that includes an gravity sensor or accelerometer that monitors or otherwise detects the orientation of the device and indicates to the user when the device is in an incorrect orientation for performing a control solution test. In one embodiment, the gravity sensor or accelerometer is integrated within the device, such as coupled to the printed circuit board of the device and housed within the housing of the device. In some instances, the gravity sensor or accelerometer is always active. In other instances, the gravity sensor or accelerometer becomes activated when a control solution test is initiated.

Methods related thereto are also provided. The methods include initiation of a control solution test; monitoring or otherwise detecting the orientation of the device by a gravity sensor or accelerometer; and indicating to the user if the orientation of the device is improper for performing the control solution test. The indication may be audible and/or visual, such as an LED or message on a display for instance. Furthermore, the monitoring and detecting of the orientation may be constantly active or activated upon initiation of a control solution test.

In some embodiments, the methods include providing instructions to the user as to the correct orientation or how to achieve the correct orientation of the device for the control solution test. The instructions may include an image (e.g., a picture of the device in the correct orientation) or a video demonstrating the correct orientation.

In some embodiments, the methods include disabling the device or otherwise not permitting the user from completing a control solution test until the device is oriented properly to prevent damage to the device.

Figure 48B:
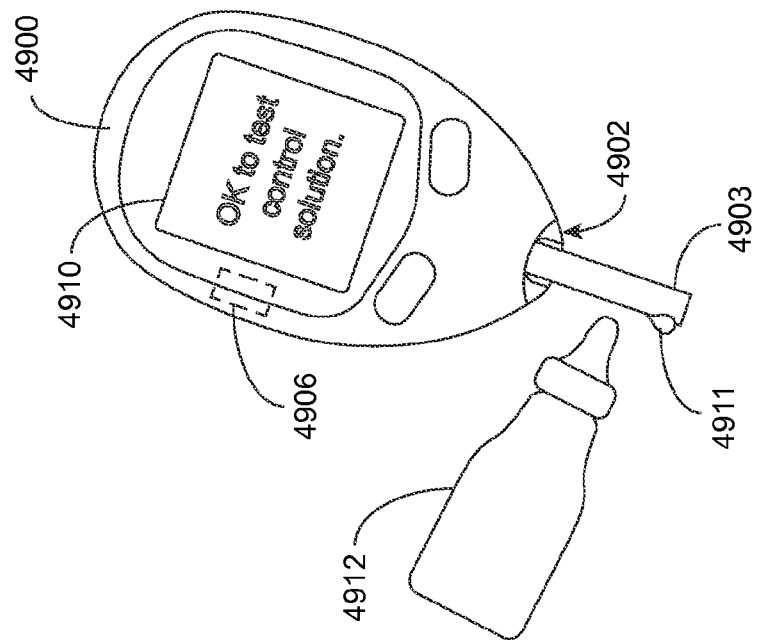
FIGS. 48A-B illustrate an analyte measurement device including a gravity sensor or accelerometer, in accordance with an embodiment presented herein.
Figure 48A:
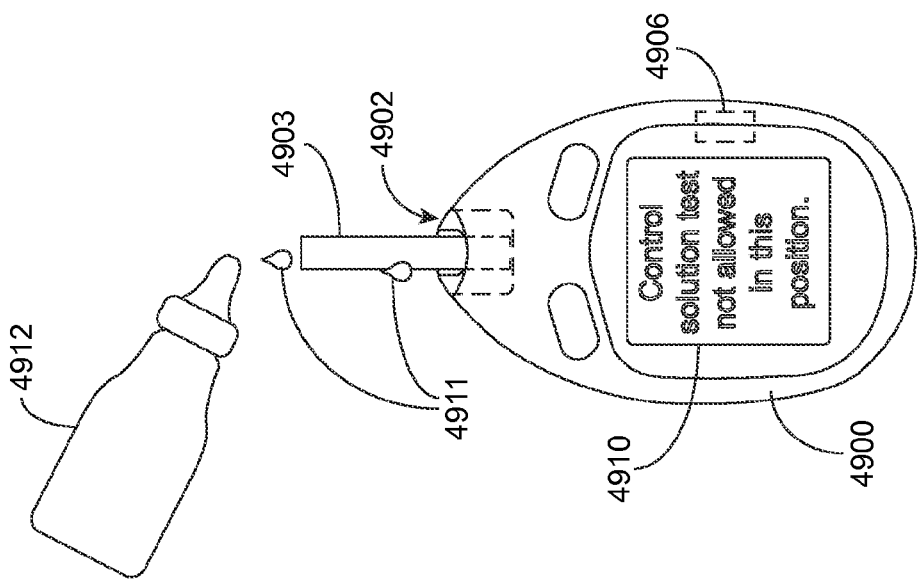

FIGS. 48A-B illustrate an analyte measurement device including a gravity sensor or accelerometer, according to one embodiment. Analyte measurement device 4900 is shown including a strip port 4902 and gravity sensor or accelerometer 4906 disposed within the device 4900. The gravity sensor or accelerometer 4906 is electrically coupled to the electronics of the analyte measurement device and in communication with other electrical components of the device 2900, such as a microprocessor (not shown).

In FIG. 48A, measurement device 4900 is oriented improperly for performing a control test solution. As shown, the strip port 4902 is oriented upward and thus gravity will draw excess or misdirected solution 4911 down into the strip port 4902. Device 4900 indicates that the device 4900 is in an improper position via a message on the display 4910. The device may also provide an audible warning to further ensure the user is warned. In one embodiment, the device does not enable the user to perform a control solution test when the device is improperly positioned.

In FIG. 48B, the user reorients the device 4900 to a proper orientation to perform a control solution test (e.g., a blood glucose measurement). The proper orientation may vary, but should avoid orientations where the strip port 4902 is positioned such that gravity draws solution 4911 toward the strip port 4902. Proper orientation may include for example, the device 4900 oriented such that gravity draws the solution 4911 away from the strip port 4902 or otherwise does not draw solution 4911 towards the strip port 4902. With the device in a proper orientation for performing a control solution test, the device 4900 indicates that the device is in a proper orientation for the test, via a message displayed on the display 4910, for example. Again, the device may also provide an audible indication that the device is properly positioned. In the embodiment where the device does not enable the user to perform a control solution test when the device is improperly positioned, the device 4900 would now enable the user to perform the test since the device is properly oriented.

Analyte Test Strips

Analyte test strips for use with the present devices can be of any kind, size, or shape known to those skilled in the art; for example, FREESTYLE® and FREESTYLE LITE™ test strips, as well as PRECISION™ test strips sold by ABBOTT DIABETES CARE Inc. In addition to the embodiments specifically disclosed herein, the devices of the present disclosure can be configured to work with a wide variety of analyte test strips, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; the disclosures of each of which are incorporated by reference herein in their entirety.

Integrated with Lancing Device

In another embodiment, an analyte measurement system may include an integrated analyte test meter and lancing device for providing a bodily fluid sample, such as a blood sample, and measuring an analyte concentration, such as a blood glucose concentration. Examples of such integrated devices include systems and devices described in US Published Application Nos. US2007/0149897 and US2008/0167578, the disclosures of each of which are incorporated herein by reference in their entirety.

Calculation of Medication Dosage

In one embodiment, the analyte measurement system may be configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function may include an algorithm or routine based on the current blood glucose concentration of a diabetic patient, to compare the current measured blood glucose concentration value to a predetermined threshold or an individually tailored threshold as determined by a doctor or other treating professional to determine the appropriate dosage level for maintaining the baseline glucose level. In one embodiment, the long-acting insulin dosage calculation function may be based upon LANTUS® insulin, available from Sanofi-Aventis, also known as insulin glargine. LANTUS® is a long-acting insulin that has up to a 24 hour duration of action. Further information on LANTUS® insulin is available at the website located by placing "www" immediately in front of ".lantus.com". Other types of long-acting insulin include Levemir® insulin available from NovoNordisk (further information is available at the website located by placing "www" immediately in front of ".levemir-us.com". Examples of such embodiments are described in in US Published Patent Application No. US2010/01981142, the disclosure of which is incorporated herein by reference in its entirety.

Docking Station

In another embodiment, the analyte measurement system may include a corresponding docking station or one or more other peripheral devices. The docking station may include, among others, a transmitter whereby when the analyte measurement system is docked to the docking station, the analyte measurement system and docking station may communicate over a data network with, for example, a healthcare provider, for the transfer of data or receipt of instructions or new dosage regimens. The docking station transmitter may be configured for transmission protocols including, but not limited to, cellular telephone transmission, such as code division multiple access (CDMA) or Global System for Mobile communications (GSM), internet communication, facsimile communications, and/or telephone communication. In another aspect, the docking station may also be configured to provide power for recharging a rechargeable battery of the analyte measurement system. In another aspect, the docking station may be configured for communication with a personal computer for additional storage, programming, and/or communication.

In another embodiment, a docking station such as described in U.S. Pat. No. 7,077,328 may be employed. As stated above, U.S. Pat. No. 7,077,328 is incorporated herein by reference in its entirety.

In some aspects of the present disclosure, a docking station is provided that serves as an information server for "docking" an analyte measurement device such, as a glucose meter, and that also provides storage and recharging capabilities for spare batteries, such as standard batteries that can be recharged. For example, the docking station may serve as a docking station for an analyte measurement devices described in the present disclosure.

Recharging batteries, such as two AA batteries, may take at least two hours to recharge, for example. If the docking station only recharges installed batteries, then the user is faced with either docking the meter and absorbing the time cost of two hours, or buying and storing a separate recharger. However, having a docking station that serves as an information server and that also provides storage and recharging capabilities for spare batteries, enables a user to switch in charged batteries from the docking station, and then place the exhausted batteries in the stations for recharging.

In one embodiment, the docking module and the battery charging module remain distinct such that existing related technologies may be applied to save development time with integration. In another embodiment, the docking module and the battery charging module are not entirely distinct.

Figure 49B:
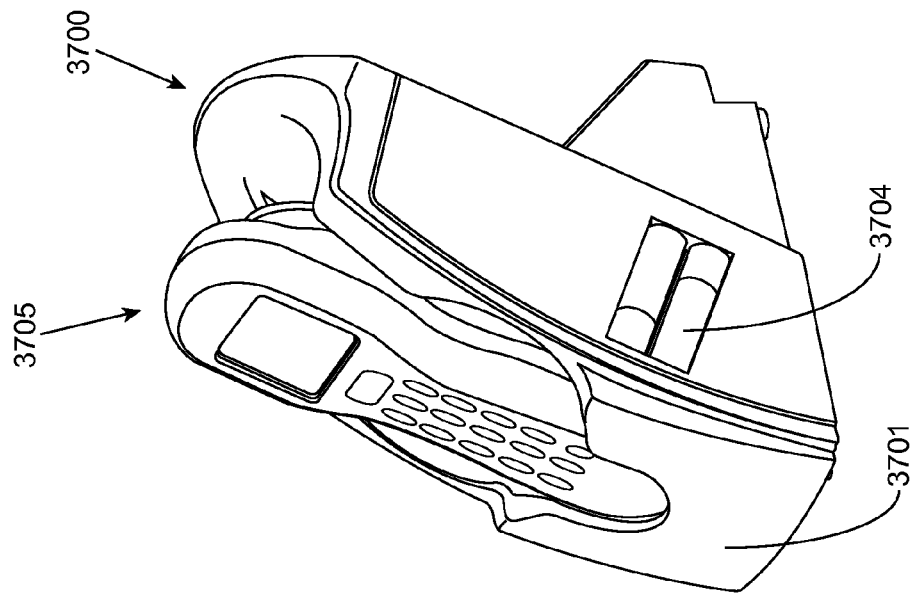
FIGS. 49A-B illustrate a docking station, in accordance with an embodiment presented herein.
Figure 49A:
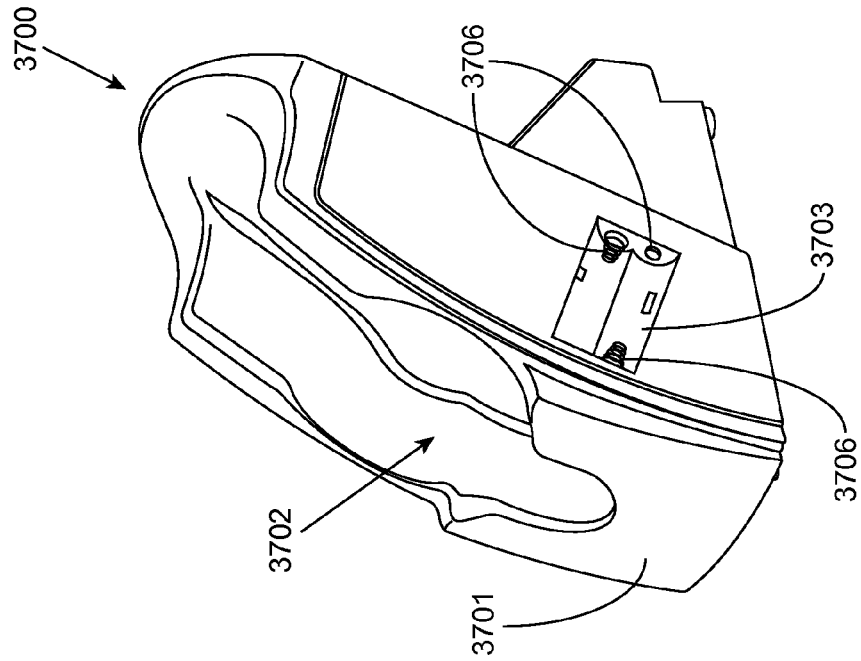

FIGS. 49A-B illustrate a docking station, according to one embodiment. Docking station 3700 includes a housing 3700 having a docking port 3702 and battery compartment 3703. Docking port 3702 is shaped to form fit with a compatible measurement device. In some instances, the docking port 3702 may be form fitted to be compatible with multiple types or models of measurement devices. The docking port 3701 includes contacts (not shown) that mate with corresponding contacts on the measurement device to electrically couple the docking station and the measurement device. In this way, the docking station may recharge the installed batteries in the measurement device when the device is docked in the docking station.

Battery compartment 3703 is disposed within housing 3701 and configured to hold one or more batteries separate from the measurement device 3705. For example, the battery compartment 3703 may be configured to hold the batteries 3704 that are required to operate the meter. In other embodiments, the battery compartment 3703 is configured to hold more batteries, such as two sets of backup batteries, or different batteries for varying models or types of measurement devices. Contacts 3706 are disposed within battery compartment 3703 and electrically couple the batteries 3704 to the docking station to enable the batteries 3704 to be charged by the docking station. The docking station 3700 includes a AC power cord, for example, to connect to an AC power source and charge the installed and separate batteries. In other embodiments, the docking station may connect to another device and receive power from the connected device, or alternatively, include its own internal power source.

Figure 49C:
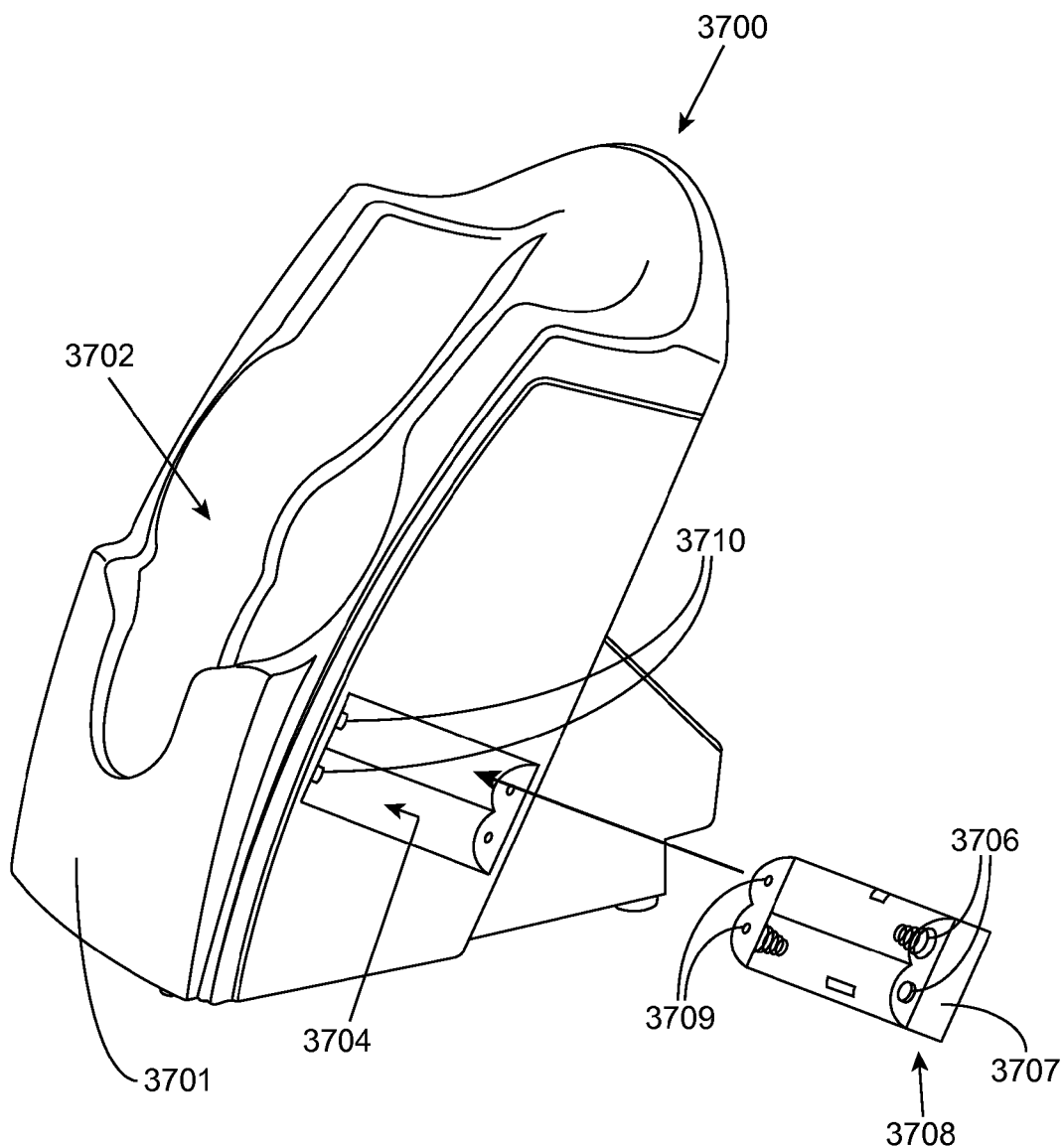
FIG. 49C illustrates a removable charging module, in accordance with an embodiment presented herein.

In one embodiment, the docking station includes a removable charging module that is removably coupled to the docking station. The removable charging module may be, for example, structurally and/or electrically separable from the docking station. For example, FIG. 49C illustrates a removable charging module, according to one embodiment. In the embodiment shown, removable charging module 3708 includes a battery compartment frame 3707 having contacts 3706 that electrically couple with the batteries 3704 when inserted within the battery compartment frame 3707 of docking station 3700. Battery compartment frame 3707 is inserted within a corresponding receptacle 3711 of docking station 3700, for example. The receptacle includes contacts 3710 that electrically mate with contacts 3709 on battery component frame 3707. Contacts 3709 are also electrically coupled to contacts 3706, which enable the docking station 3700 to electrically couple to batteries within the battery compartment frame 3707 and recharge them.

It should be appreciated that in some embodiments more than one removable charging module may be disposed within the docking station. Further, in some instances, the docking station may be configured to receive and operate with more than one type of removable recharging module, such as removable charging modules from different measurement devices and/or different redesigns and/or models. In some instances, the removable charging module may be off-the-shelf and/or derived from off-the shelf recharging stations.

Strip Port Configured to Receive Test Strips for Different Analytes

In another embodiment, there is provided an analyte measurement system for multichemistry testing. The test strips are for chemical analysis of a sample, and are adapted for use in combination with a measuring device having a test port and capable of performing a multiplicity of testing functionalities. Each type of test strip corresponds to at least one of the testing functionalities, and at least some types of test strips have indicators of the testing functionality on them. The test port is adapted for use in combination with a multiplicity of different types of test strips and includes a sensor capable of specifically interacting with the indicator(s) on the test strips, thereby selecting at least one of the multiplicity of testing functionalities corresponding to the type of test strip. Such system would include a strip port that can be used to read a test strip for glucose and a test strip for ketone bodies. Examples of such embodiment are provided in U.S. Pat. No. 6,773,671, which is incorporated herein by reference in its entirety.

Strip Port Configured to Receive Test Strips Having Different Dimensions and/or Electrode Configurations In some embodiments, an analyte measurement system as described herein includes a strip port configured to receive test strips having different dimensions and/or electrode configurations, e.g., as described in the U.S. patent application Ser. No. 12/695,947 filed on Jan. 28, 2010, and entitled "Universal Test Strip Port", the disclosure of which is incorporated by reference herein in its entirety.

Test Strip Ejector

In some embodiments, an analyte measurement system as described herein is configured to include an optional analyte test strip ejector configured to eject an analyte test strip from a test strip port of the analyte measurement system. An analyte test strip ejector may be useful, for example, where it is desirable to eject an analyte test strip containing a sample of bodily fluid, e.g., blood, following an analyte measurement conducted using the analyte measurement system. This allows a user of the analyte measurement system to dispose of the contaminated analyte test strip without touching the analyte test strip.

In some embodiments, the analyte test strip ejector slidably engages a portion of the housing of the analyte measurement system. The analyte test strip ejector may be configured such that upon insertion of an analyte test strip into the test strip port, the analyte test strip ejector is moved rearward with respect to the test strip port and in the direction of insertion. In order to eject the analyte test strip, a user physically moves the analyte test strip ejector forward with respect to the test strip port and in the opposite of the direction of insertion. This movement in-turn exerts force upon the analyte test strip expelling it from the test strip port. Alternatively, the analyte test strip ejector may be configured such that insertion of the analyte test strip into a strip port of the analyte measurement system positions the analyte test strip ejector in a "cocked" position, e.g., by engaging a spring mechanism. The analyte measurement system may include a button, switch, or other suitable mechanism for releasing the cocked ejector from the cocked position such that it ejects the analyte test strip from the strip port of the analyte measurement system. Additional information regarding analyte test strip ejectors is provided in the U.S. patent application Ser. No. 12/695,947, filed on Jan. 28, 2010, and entitled "Universal Test Strip Port."

Splash-Proof Test Strip Port

In some embodiments, an analyte measurement system as described herein is configured to include a contamination resistant test strip port and/or a splash-proof test strip port. In one such embodiment, the test strip port includes one or more sealing members positioned so as to limit and/or prevent internal contamination of the test strip port with fluids and/or particles present in the environment outside the test strip port. In another embodiment, the test strip port includes an internal beveled face which can limit and/or prevent ingress of one or more external contaminants into the internal area of the test strip port.

Additional disclosure and examples of contamination resistant test strip ports are provided in U.S. patent application Ser. No. 12/539,217, filed Aug. 11, 2009, and entitled "Analyte Sensor Ports," the disclosure of which is incorporated by reference herein in its entirety.

In some embodiments, the test strip ports described herein can be configured to work with (e.g., engage with or operate in connection with) additional mechanisms and/or devices designed to limit and/or prevent contamination of the internal areas of the test strip ports themselves or the internal areas of the analyte measurement system into which the test strip ports can be integrated. For example, mechanisms, devices and methods of protecting test strip port openings are described in U.S. Patent Application Publication No. US2008/0234559, and U.S. Patent Application Publication No. US2008/0119709, the disclosure of each of which is incorporated by reference herein in their entirety. Test strip ports according to the present disclosure can also be configured to be replaceable and/or disposable, and/or configured so as to limit and/or prevent contamination of the analyte measurement system in which the test strip port is integrated. Additional description is provided, for example, in U.S. Application Publication No. 2010/0064800, the disclosure of which is incorporated by reference herein it its entirety.

Implanted Analyte Sensor

In some embodiments, an analyte measurement system as described herein may include an implanted or partially implanted analyte sensor, e.g., a system including an implanted or partially implanted glucose sensor (e.g., a continuous glucose sensor). A system including an implanted or partially implanted glucose sensor may include an analyte measurement system as described herein, which is configured to receive analyte data from the implanted or partially implanted glucose sensor either directly or through an intermediate device, e.g., an RF-powered measurement circuit coupled to an implanted or partially implanted analyte sensor. In some embodiments, where an analyte measurement system according to the present disclosure is integrated with an implanted sensor, the analyte measurement system does not include a strip port for receiving an analyte test strip. In one embodiment, the analyte measurement system may be used to calibrate the analyte monitoring system, e.g., using one point calibration or other calibration protocol. For additional information, see U.S. Pat. No. 6,175,752, the disclosure of which is incorporated by reference herein in its entirety. In some embodiments, the analyte measurement system may be configured to communicate with the implanted or partially implanted analyte sensor via Radio Frequency Identification (RFID) and provide for intermittent or periodic interrogation of the implanted analyte sensor.

Exemplary analyte monitoring systems that may be utilized in connection with the disclosed analyte measurement system include those described in U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; and U.S. provisional application No. 61/149,639 titled "Compact On-Body Physiological Monitoring Device and Methods Thereof", the disclosures of each of which are incorporated herein by reference in their entirety.

Integration with Medication Delivery Devices and/or Systems

In some embodiments, the analyte measurement systems disclosed herein may be included in and/or integrated with, a medication delivery device and/or system, e.g., an insulin pump module, such as an insulin pump or controller module thereof. In some embodiments the analyte measurement system is physically integrated into a medication delivery device. In other embodiments, an analyte measurement system as described herein may be configured to communicate with a medication delivery device or another component of a medication delivery system. Additional information regarding medication delivery devices and/or systems, such as, for example, integrated systems, is provided in U.S. Patent Application Publication No. US2006/0224141, published on Oct. 5, 2006, entitled "Method and System for Providing Integrated Medication Infusion and Analyte Monitoring System", and U.S. Patent Application Publication No. US2004/0254434, published on Dec. 16, 2004, entitled "Glucose Measuring Module and Insulin Pump Combination," the disclosure of each of which is incorporated by reference herein in its entirety. Medication delivery devices which may be provided with analyte measurement system as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte measurement system. Additional information is provided in U.S. Pat. Nos. 5,536,249 and 5,925,021, the disclosures of each of which are incorporated by reference herein in their entirety.

Communication Interface

As discussed previously herein, an analyte measurement system according to the present disclosure can be configured to include a communication interface. In some embodiments, the communication interface includes a receiver and/or transmitter for communicating with a network and/or another device, e.g., a medication delivery device and/or a patient monitoring device, e.g., a continuous glucose monitoring device. In some embodiments, the communication interface is configured for communication with a health management system, such as the CoPilot™ system available from Abbott Diabetes Care Inc., Alameda, Calif.

The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the analyte measurement system and other external devices such as a computer terminal (for example, at a physician's office or in hospital environment), an external medical device, such as an infusion device or including an insulin delivery device, or other devices that are configured for similar complementary data communication.

In one embodiment, the communication interface is configured for infrared communication, Bluetooth® communication, or any other suitable wireless communication protocol to enable the analyte measurement system to communicate with other devices such as infusion devices, analyte monitoring devices, computer terminals and/or networks, communication enabled mobile telephones, personal digital assistants, or any other communication devices which the patient or user of the analyte measurement system may use in conjunction therewith, in managing the treatment of a health condition, such as diabetes.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the analyte measurement system is configured to wirelessly communicate with a server device via the communication interface, e.g., using a common standard such as 802.11 or Bluetooth® RF protocol, or an IrDA infrared protocol. The server device could be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the analyte measurement system indirectly by interacting with the user interface(s) of the server device, which in turn interacts with the analyte measurement system across a wireless link.

In some embodiments, the communication interface is configured to automatically or semi-automatically communicate data stored in the analyte measurement system, e.g., in an optional data storage unit, with a network or server device using one or more of the communication protocols and/or mechanisms described above.

Input Unit

As discussed previously herein, an analyte measurement system according to the present disclosure can be configured to include an input unit and/or input buttons coupled to the housing of the analyte measurement system and in communication with a controller unit and/or processor. In some embodiments, the input unit includes one or more input buttons and/or keys, wherein each input button and/or key is designated for a specific task. Alternatively, or in addition, the input unit may include one or more input buttons and/or keys that can be 'soft buttons' or 'soft keys'. In the case where one or more of the input buttons and/or keys are 'soft buttons' or 'soft keys', these buttons and/or keys may be used for a variety of functions. The variety of functions may be determined based on the current mode of the analyte measurement system, and may be distinguishable to a user by the use of button instructions shown on an optional display unit of the analyte measurement system. Yet another input method may be a touch-sensitive display unit, as described in greater detail below.

In addition, in some embodiments, the input unit is configured such that a user can operate the input unit to adjust time and/or date information, as well as other features or settings associated with the operation of an analyte measurement system.

Display Unit

As discussed previously herein, in some embodiments, an analyte measurement system according to the present disclosure includes an optional display unit or a port for coupling an optional display unit to the analyte measurement system. The display unit is in communication with a control unit and/or processor and displays the analyte test strip signals and/or results determined from the analyte test strip signals including, for example, analyte concentration, rate of change of analyte concentration, and/or the exceeding of a threshold analyte concentration (indicating, for example, hypo- or hyperglycemia).

The display unit can be a dot-matrix display, e.g., a dot-matrix LCD display. In some embodiments, the display unit includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit can be configured to provide, an alphanumeric display, a graphical display, a video display, an audio display, a vibratory output, or combinations thereof. The display can be a color display. In some embodiments, the display is a backlit display.

The display unit can also be configured to provide, for example, information related to a patient's current analyte concentration as well as predictive analyte concentrations, such as trending information.

In some embodiments an input unit and a display unit are integrated into a single unit, for example, the display unit can be configured as a touch sensitive display, e.g., a touch-screen display, where the user may enter information or commands via the display area using, for example, the user's finger, a stylus or any other suitable implement, and where, the touch sensitive display is configured as the user interface in an icon driven environment, for example.

In some embodiments, the display unit does not include a screen designed to display results visually. Instead, in some embodiments the optional display unit is configured to communicate results audibly to a user of the analyte measurement system, e.g., via an integrated speaker, or via separate speakers through a headphone jack or Bluetooth® headset.

Expanding Menu Item for Improved Readability

In some embodiments, the display unit includes a graphical user interface including a plurality of menu items, wherein the display unit is configured to provide clarification with respect to the meaning of a menu item based on a user's response speed with respect to a user input for the menu item. The menu item could take any of a variety of forms, e.g., text, icon, object or combination thereof.

In one embodiment, the graphical user interface includes a menu which in turn includes a plurality of selectable menu items. As a user navigates through the menu, e.g., by highlighting or scrolling through individual menu items, a menu item that is either unreadable or incomprehensible to the user could cause the user to pause over a menu item to be selected. In one embodiment, a choice can be presented to the user, e.g., using a dedicated physical button on an input unit, or a soft key on the menu, that offers further explanation of the item to be selected without actually selecting the item. For example, the graphical user interface can be configured such that after a pre-determined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care provider, or through an adaptive mechanism based on an analysis of the user's speed of navigation from past interactions with the graphical user interface. In one embodiment, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Support for on-Demand Analyte Determination Using an Analyte Sensor

In some embodiments, an analyte measurement system according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. An analyte measurement system according to the present disclosure may include software configured to analyze signals received from the analyte sensor. Additional information related to self-powered analyte sensors and methods of communicating therewith are provided in U.S. Patent Application Publication No. 2010/0213057, the disclosure of which is incorporated by reference herein in its entirety.

Integrated Bar Code

In an embodiment, an analyte measurement system according to the present disclosure is integrated with a barcoding system. The barcoding system may be laser or LED based, and may be used for identification of analyte test strips, patient, health care professional, etc. For example, the analyte measurement system may include a barcode reader disposed in the housing. The housing would further require an internal circuitry and a barcode scan engine for processing of a scan. Additional examples of such a bar coding system is provided in U.S. Pat. No. 7,077,328, which has been incorporated herein by reference in its entirety.

Anti-Microbial Thin Film Cover

In an embodiment, an analyte measurement system according to the present disclosure is provided with an anti-microbial thin film cover. A common problem with many analyte measurement systems is that the housing cracks, degrades, and generally wears down due to the harsh chemicals that are used to disinfect the analyte measurement system in hospital and clinical environments. By placing an anti-microbial plastic film over the analyte measurement system, the life-cycle of the system can be prolonged because the plastic film is subjected to the disinfectants, rather than the system housing itself. When the plastic film begins to degrade, it can be removed and replaced. The plastic film also adds an additional layer of sterility to the system. The plastic film may be transparent, and applied over the display and/or user interface. One side of the plastic film would contain anti-microbial chemistry, while the back side of the plastic film would contain a thin layer of adhesive.

Analytes

A variety of analytes can be detected and quantified using the disclosed analyte measurement system. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006 and U.S. Pat. No. 6,638,716, the disclosures of each of which are incorporated by reference herein in their entirety.

CONCLUSION

The foregoing description of the subject matter of the present disclosure has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. An analyte measurement system, comprising:
   an analyte meter having a meter housing and a processing circuit disposed within the housing; and
   a replaceable strip port module having:
   a module housing, wherein the module housing includes a first aperture that receives an analyte test strip, and an interface aperture,
   an analyte test strip port disposed within the module housing, wherein the analyte test strip port comprises electrical contacts that couple to an analyte test strip positioned in the first aperture of the module housing, and
   an electrical interface coupled to the analyte test strip port that electrically couples to the analyte meter through the interface aperture of the module housing, and comprising a plurality of contact pads configured to couple to electrical connections within the meter housing.

2. The analyte measurement system of claim 1, further comprising an attachment feature to removably attach the replaceable strip port module to the analyte meter.

3. The analyte measurement system of claim 1, wherein the module housing fits within an aperture in the meter housing.

4. The analyte measurement system of claim 3, wherein the module housing includes external alignment features to align the module housing within the aperture in the meter housing.

5. The analyte measurement system of claim 3, wherein the meter housing includes alignment features to align the module housing within the aperture in the meter housing.

6. The analyte measurement system of claim 1, wherein the electrical interface includes a plurality of pins to couple to a pin header within the meter housing.

7. The analyte measurement system of claim 1, wherein the electrical interface includes an edge connector to couple to a corresponding edge connector within the meter housing.

8. A replaceable strip port module for use in a modular analyte measurement system, comprising:
   a housing, wherein the housing includes an open end and an interface aperture;
   an analyte test strip port disposed within the open end of the housing and comprising electrical contacts;
   an electrical interface coupled to the analyte test strip port within the housing and positioned such that the electrical interface is exposed to the exterior of the housing through the interface aperture and wherein the electrical interface is configured to electrically couple to an analyte meter through the interface aperture of the housing and comprises a plurality of contact pads configured to couple to electrical connections within an analyte meter; and
   a cap covering the open end of the housing, wherein the cap includes an aperture sized to receive an analyte test strip, and wherein the aperture is aligned with the analyte test strip port such that when an analyte test strip is inserted into the aperture, the analyte test strip is inserted into the analyte test strip port; and
   wherein, when the analyte test strip is positioned in the aperture in the cap and the test strip port, the electrical contacts of the analyte test strip port couple to the analyte test strip.

9. The replaceable strip port module of claim 8, wherein the housing further comprises internal alignment features to align the analyte test strip port within the housing.

10. The replaceable strip port module of claim 8, wherein the housing further comprises external alignment features to align the replaceable strip port module within an analyte meter in the analyte measurement system.

11. The replaceable strip port module of claim 8, wherein the electrical interface includes a plurality of pins to couple to a pin header within an analyte meter.

12. The replaceable strip port module of claim 8, wherein the electrical interface includes an edge connector to couple with a corresponding edge connector within an analyte meter.

13. The replaceable strip port module of claim 8, wherein the cap includes an indented region on a surface of the cap.

14. The replaceable strip port module of claim 8, wherein a cap gasket is provided as a seal between the cap and an analyte meter.

15. The replaceable strip port module of claim 14, wherein a second cap gasket is provided as a seal between the cap and the housing.

16. The replaceable strip port module of claim 8, wherein a single cap gasket is provided as a seal between the cap, the housing, and an analyte meter.

17. The analyte measurement system of claim 1, wherein the contact pads of the electrical interface electrically couple to the analyte test strip port and the analyte meter.

18. The replaceable strip port module of claim 8, wherein the cap is configured to removably attach from the housing of an analyte meter.

* * * * *